United States Patent
Von Schaewen (12)

(10) Patent No.: US 6,653,459 B1
(45) Date of Patent: Nov. 25, 2003

(54) PLANT GNTI SEQUENCES AND THE USE THEREOF FOR THE PRODUCTION OF PLANTS HAVING REDUCED OR LACKING N-ACETYL GLUCOSAMINYL TRANSFERASE I(GNTI) ACTIVITY

(76) Inventor: Antje Von Schaewen, Natruper Strasse 169A, 49076, Osnabrück (DE)

( * ) Notice: Subject to any disclaimer, the term of this patent is extended or adjusted under 35 U.S.C. 154(b) by 0 days.

(21) Appl. No.: 09/591,466

(22) Filed: Jun. 9, 2000

Related U.S. Application Data

(63) Continuation of application No. PCT/EP98/08001, filed on Dec. 9, 1998.

(30) Foreign Application Priority Data

Dec. 9, 1997 (DE) .......................................... 197 54 622

(51) Int. Cl.$^7$ ........................... C07H 21/04; C12Q 1/68

(52) U.S. Cl. ................... 536/23.1; 536/24.3; 536/23.6; 800/278; 800/295; 435/6; 435/320.1; 435/410

(58) Field of Search ................................ 800/295, 278; 435/6, 320.1, 410; 536/23.1, 24.3, 23.6

(56) References Cited

FOREIGN PATENT DOCUMENTS

| WO | WO 92/09694 | 6/1992 |
|----|-------------|--------|
| WO | WO 96/21038 | 7/1996 |

OTHER PUBLICATIONS

Chemical Abstracts 119: 245692f.
Chemical Abstracts 120: 294245s.
EML–Genbank AC B24856.
EML–Genbank AC AC000098.
Altmann, F., et al. "Processing of asparagine–linked oligosaccharides in insect cells. N–acetylglucosaminyl transferase I and II activities in cultured lepidopteran cells." *Glycobiology* 3: 619–625 (1993).
Barton, N.W., et al. "Therapeutic response to intravenous infusions of glucocerebrosidase in a patient with Gaucher disease." *Proc Natl Acad Sci USA.* 87: 1913–1916 (1990).
Bevan, M. "Binary Agrobacterium vectors for plant transformation." *Nucl. Acids Res.* 12: 8711–8721 (1984).
Church, G.M., et al. "Genomic sequencing." *Proc Acad Sci USA* 81: 1991–1995 (1984).
Damm, B., et al. "Efficient transformation of *Arabidopsis thaliana* using direct gene transfer to protoplasts." *Mot Gen Genet.* 213: 15–20 (1989).
Deblaere, R., et al. "Efficient octopine Ti plasmid–derived vectors for Agrobacterium mediated gene transfer to plants." *Nucl Acids Res.* 13: 4777–4788 (1985).
Dennis, J.W., et al. "β→6 branching of Asn–linked oligosaccharides is directly associated with metastasis." *Science* 236: 582–585 (1987).

Faske, M, et al. "Transgenic tobacco plants expressing pea chloroplast Nmdh cDNA in sense and antisense orientation: Effects on NADP–MDH level, stability of transformants, and plant growth." *Plant Physiol.* 115: 705–715 (1997).
Faye, L., et al. "Apparent inhibition of βfructosidase secretion by tunicamycin may be explained by breakdown of the unglycosylated protein during secretion." *Plant Physiol* 89: 845–851 (1989).
Fukuda, M.N. "HEMPAS disease: genetic defect of glycosylation." *Glycobiology* 1: 9–15 (1990).
Fukuda, M.N., et al. "Incomplete synthesis of N–glycans in congenital dyserythropoetic anemia type II caused by a defect in the gene encoding α–mannosidase II." *Proc Natl Acad Sci USA* 87: 7443–7447 (1990).
Gomez, L, et al. "Complementation of an *Arabidopsis thaliana* mutant that lacks complex asparagine–linked glycans with the human cDNA encoding –acetylglucosaminyl–transferase I." *Proc. Natl. Acad. Sci. USA.* 91: 1829–1833 (1994).
Graeve, K., et al. "Purification, characterization and cDNA sequence of glucose–6–phosphate dehydrogenase from potato (*Solanum tuberosum* L.)." *Plant J.* 5: 353–361 (1994).
Harlow, E., et al. *Antibodies: A Laboratory Manual*, Cold Spring Harbor Laboratory Press, Cold Spring Harbor, NY (1988).
Hildmann, T., et al. "General roles of abscisic and jasmonic acids in gene activation as a result of mechanical wounding." *Plant Cell* 4: 1157–1170 (1992).
Höfgen, R., et al. "Storage of competent cells for Agrobacterium transformation." *Nucl Acids Res.* 16: 9877 (1988).
Höfte, H., et al. "The protein–body proteins phytohemagglutinin and tonoplast intrinsic protein are targeted to vacuoles in leaves of transgenic tobacco." *Planta.* 184: 431–437 (1991).
Johnson, K.D., et al. "Substrate specificities of N–acetylglucosaminyl–, fucosyl–, and xylosyltransferases that modify glycoproteins in the Golgi apparatus of bean cotyledons." *Plant Physiol.* 84: 1301–1308 (1987).

(List continued on next page.)

Primary Examiner—W. Gary Jones
Assistant Examiner—Jeanine Goldberg
(74) Attorney, Agent, or Firm—Burns, Doane, Swecker & Mathis, L.L.P.

(57) ABSTRACT

This invention relates to plant GntI sequences, in particular to plant nucleic acid sequences encoding the enzyme N-acetyl glucosaminyl transferase I (GnTI), DNA sequences derived therefrom, including GntI antisense and sense constructs, and the translation products thereof, antibodies directed against said translation products, as well as the use of the sequence information for the production of transformed microorganisms and transgenic plants, including those having reduced or missing N-acetyl glucosaminyl transferase I activity. Such plants displaying reduced or lacking N-acetyl glucosaminyl transferase I activity are of great importance for the production of glycoproteins of specific constitution with respect to their sugar residues.

4 Claims, 6 Drawing Sheets

OTHER PUBLICATIONS

Kaushal, GP, et al.. "Structure and biosynthesis of plant N–linked glycans." J Preiss, Ed. *The Biochemistry of Plants*, vol. 14: Carbohydrates. Academic Press, San Diego, CA, (1988) pp 421–463.

Koes, K., et al. "Targeted gene inactivation in petunia by PCR–based selection of transposon insertion mutants." *Proc Acad Sci USA* 92: 8149–8153 (1995).

Kornfeld, R., et al. "Assembly of asparagine–linked oligosaccharides." *Annu Rev Biochem* 54: 631–664 (1985).

Kumar, R., et al. "Cloning and expression of N –acetylglucosaminyltransferase I, the medial Golgi transferase that initiates complex N–linked carbohydrate formation." *Proc Natl Acad Sci USA* 87: 9948–9952 (1990).

Laurière, M., et al. "Characterization of a xylose–specific antiserum that reacts with the complex asparagine–linked glycans of extracellular and vacuolar glycoproteins." *Plant Physiol.* 90: 1182–1188 (1989).

Ma, JK–C, et al. "Plant antibodies for immunotherapy." *Plant Physiol.* 109: 341–346 (1995).

McKinney, E.C., et al. "Sequence–based identification of T–DNA insertion mutations in Arabidopsis: actin mutants act2–1 and act4–1." *Plant J.* 8: 613–622 (1995).

Moffat, AS . "Medical applications: Exploring transgenic plants as a new vaccine source." *Science* 268: 658–660 (1995) (summary of two original publications in the same issue).

Olden, K., et al. "Function of glycoprotein glycans." *Trends Biochem Sci* 10: 78–82 (1985).

Puchta, H., et al. "From centiMorgans to base pairs: homologous recombination in plants." *Plant Sci.* 1: 340–348 (1996).

Rademacher, T.W., et al. "Glycobiology." *Annu Rev Biochem* 57: 785–838 (1988).

Rocha–Sosa, M., et al. "Both developmental and metabolic signals activate the promoter of a class I patatin gene." *EMBO J.* 8: 23–29 (1989).

Sambrook, J., et al. *Molecular cloning: a laboratory manual* (2nd edn), Cold Spring Harbor Laboratory, Cold Spring Harbor, NY (1989).

Schmidt, T.G.M., et al. "The random peptide library assisted engineering of a C–terminal affinity peptide, useful for the detection and purification. of a functional Ig Fv fragment." *Prot Engineering.* 6: 109–122 (1993).

Sorge, J., et al. "Molecular cloning and nucleotide sequence of human cerebrosidase cDNA." *Proc Natl Acad Sci USA*. 82: 7289–7293 (1985).

Stanley, P. "Chinese hamster ovary cell mutants with multiple glycosylation defects for production of glycoproteins with minimal carbohydrate heterogeneity." *Mol Cell Biol* 9:377–383 (1989).

Sturm, A., et al. "Subcellular localization of glycosidases and glycosyltransferases involved in the processing of N–linked oligosaccharides." *Plant Physiol.* 85: 741–745 (1987).

Sturm, A. "Heterogeneity of the complex N–linked oligosaccharides at specific glycosylation sites of 2 secreted carrot glycoproteins." *Eur J Biochem* 199: 169–179 (1991).

Taylor, CB. "Comprehending cosuppression." *Plant Cell* 9: 1245–1249 (1997)(summary of several original publications in the same issue).

Van der Wilden, M., et al. "The endoplasmic reticulum of mung bean cotyledons: role in the accumulation of hydrolases in protein bodies during seedling growth." *Plant Physiol.* 66: 390–394 (1980).

Voelker, T., et al. "Differences in expression between two seed lectin alleles obtained from normal and lectin–deficient beans are maintained in transgenic tobacco." *EMBO J.* 6: 3571–3577 (1987).

Von Schaewen, A., et al. "Expression of a yeast–derived invertase in the cell wall of tobacco and Arabidopsis plants lead to accumulation of carbohydrate, inhibition of photosynthesis and strongly influences growth and phenotype of transgenic tobacco plants." *EMBO J..* 9: 3033–3044 (1990).

Von Schaewen, A., et al. "Isolation of a mutant Arabidopsis plant that lacks N–acetyl glucosaminyl transferase I and is unable to synthesize Golgi–modified complex N–linked glycans." *Plant Physiol.* 102: 1109–1118 (1993).

Figure 2

A1 *GntI* cDNA

```
GAATTCGCGG CCGCCTGAGA AACCCTCGAA TTCAATTTCG CATTTGGCAG AG ATG                55
                                                          Met
                                                          1

AGA GGG AAC AAG TTT TGC TTT GAT TTA CGG TAC CTT CTC GTC GTG GCT             103
Arg Gly Asn Lys Phe Cys Phe Asp Leu Arg Tyr Leu Leu Val Val Ala
            5               10                  15

GCT CTC GCC TTC ATC TAC ATA CAG ATG CGG CTT TTC GCG ACA CAG TCA             151
Ala Leu Ala Phe Ile Tyr Ile Gln Met Arg Leu Phe Ala Thr Gln Ser
            20              25                  30

GAA TAT GTA GAC CGC CTT GCT GCT GCA ATT GAA GCA GAA AAT CAT TGT             199
Glu Tyr Val Asp Arg Leu Ala Ala Ala Ile Glu Ala Glu Asn His Cys
        35              40                  45

ACA AGT CAG ACC AGA TTG CTT ATT GAC AAG ATT AGC CAG CAG CAA GGA             247
Thr Ser Gln Thr Arg Leu Leu Ile Asp Lys Ile Ser Gln Gln Gln Gly
50              55                  60                  65

AGA GTA GTA GCT CTT GAA GAA CAA ATG AAG CAT CAG GAC CAG GAG TGC             295
Arg Val Val Ala Leu Glu Glu Gln Met Lys His Gln Asp Gln Glu Cys
                70          ↑    75                  80

CGG CAA TTA AGG GCT CTT GTT CAG GAT CTT GAA AGT AAG GGC ATA AAA             343
Arg Gln Leu Arg Ala Leu Val Gln Asp Leu Glu Ser Lys Gly Ile Lys
            85                  90                  95

AAG TTA ATC GGA GAT GTG CAG ATG CCA GTG GCA GCT GTA GTT GTT ATG             391
Lys Leu Ile Gly Asp Val Gln Met Pro Val Ala Ala Val Val Val Met
            100                 105                 110

GCT TGC AGT CGT ACT GAC TAC CTG GAG AGG ACT ATT AAA TCC ATC TTA             439
Ala Cys Ser Arg Thr Asp Tyr Leu Glu Arg Thr Ile Lys Ser Ile Leu
    115                 120                 125

AAA TAC CAA ACA TCT GTT GCA TCA AAA TAT CCT CTT TTC ATA TCC CAG             487
Lys Tyr Gln Thr Ser Val Ala Ser Lys Tyr Pro Leu Phe Ile Ser Gln
130                 135                 140                 145

GAT GGA TCA AAT CCT GAT GTA AGA AAG CTT GCT TTG AGC TAT GGT CAG             535
Asp Gly Ser Asn Pro Asp Val Arg Lys Leu Ala Leu Ser Tyr Gly Gln
                150                 155                 160

CTG ACG TAT ATG CAG CAC TTG GAT TAT GAA CCT GTG CAT ACT GAA AGA             583
Leu Thr Tyr Met Gln His Leu Asp Tyr Glu Pro Val His Thr Glu Arg
            165                 170                 175

CCA GGG GAA CTG GTT GCA TAC TAC AAG ATT GCA CGT CAT TAC AAG TGG             631
Pro Gly Glu Leu Val Ala Tyr Tyr Lys Ile Ala Arg His Tyr Lys Trp
            180                 185                 190

GCA TTG GAT CAG CTG TTT CAC AAG CAT AAT TTT AGC CGT GTT ATC ATA             679
Ala Leu Asp Gln Leu Phe His Lys His Asn Phe Ser Arg Val Ile Ile
    195                 200             *   205

CTA GAA GAT GAT ATG GAA ATT GCT GCT GAT TTT TTT GAC TAT TTT GAG             727
Leu Glu Asp Asp Met Glu Ile Ala Ala Asp Phe Phe Asp Tyr Phe Glu
210                 215                 220                 225
```

Figure 2 (continued)

```
GCT GGA GCT ACT CTT CTT GAC AGA GAC AAG TCG ATT ATG GCT ATT TCT      775
Ala Gly Ala Thr Leu Leu Asp Arg Asp Lys Ser Ile Met Ala Ile Ser
                230                 235                 240

TCT TGG AAT GAC AAT GGA CAA AGG CAG TTC GTC CAA GAT CCT GAT GCT      823
Ser Trp Asn Asp Asn Gly Gln Arg Gln Phe Val Gln Asp Pro Asp Ala
                245                 250                 255

CTT TAC CGC TCA GAC TTT TTT CCT GGT CTT GGA TGG ATG CTT TCA AAA      871
Leu Tyr Arg Ser Asp Phe Phe Pro Gly Leu Gly Trp Met Leu Ser Lys
                260                 265                 270

TCA ACT TGG TCC GAA CTA TCT CCA AAG TGG CCA AAG GCT TAC TGG GAT      919
Ser Thr Trp Ser Glu Leu Ser Pro Lys Trp Pro Lys Ala Tyr Trp Asp
            275                 280                 285

GAC TGG CTA AGG CTG AAA GAA AAT CAC AGA GGT CGA CAA TTT ATT CGC      967
Asp Trp Leu Arg Leu Lys Glu Asn His Arg Gly Arg Gln Phe Ile Arg
290                 295                 300                 305

CCA GAA GTT TGC AGA ACG TAC AAT TTT GGT GAG CAT GGT TCT AGT TTG     1015
Pro Glu Val Cys Arg Thr Tyr Asn Phe Gly Glu His Gly Ser Ser Leu
                310                 315                 320

GGG CAG TTT TTT AAG CAG TAT CTT GAG CCA ATT AAG CTA AAT GAT GTC     1063
Gly Gln Phe Phe Lys Gln Tyr Leu Glu Pro Ile Lys Leu Asn Asp Val
                325                 330                 335

CAG GTT GAT TGG AAG TCA ATG GAC CTA AGT TAC CTT TTG GAG GAC AAC     1111
Gln Val Asp Trp Lys Ser Met Asp Leu Ser Tyr Leu Leu Glu Asp Asn
                340                 345                 350

TAT GTG AAA CAC TTT GGC GAC TTG GTT AAA AAG GCT AAG CCC ATC CAC     1159
Tyr Val Lys His Phe Gly Asp Leu Val Lys Lys Ala Lys Pro Ile His
            355                 360                 365

GGA GCT GAT GCT GTT TTG AAA GCA TTT AAC ATA GAT GGT GAT GTG CGT     1207
Gly Ala Asp Ala Val Leu Lys Ala Phe Asn Ile Asp Gly Asp Val Arg
370                 375                 380                 385

ATT CAG TAC AGA GAC CAA CTA GAC TTT GAA GAT ATC GCT CGA CAG TTT     1255
Ile Gln Tyr Arg Asp Gln Leu Asp Phe Glu Asp Ile Ala Arg Gln Phe
                390                 395                 400

GGC ATT TTT GAA GAA TGG AAG GAT GGT GTA CCA CGG GCA GCA TAT AAA     1303
Gly Ile Phe Glu Glu Trp Lys Asp Gly Val Pro Arg Ala Ala Tyr Lys
                405                 410                 415

GGG ATA GTA GTT TTC CGG TTT CAA ACA TCT AGA CGT GTG TTC CTT GTT     1351
Gly Ile Val Val Phe Arg Phe Gln Thr Ser Arg Arg Val Phe Leu Val
                420                 425                 430

TCC CCT GAT TCT CTT CGA CAA CTT GGA GTT GAA GAT ACT TAG             1393
Ser Pro Asp Ser Leu Arg Gln Leu Gly Val Glu Asp Thr End
            435                 440                 445

CGAAGATATG ATTGGAGCCT GAGCAACAAT TTAGACTTAT TTGGTAGGAT ACATTTGAAA   1453

GAGCTGACAC GAAAAGTATG ACTACCAGTA GCTACATGCA ACATTTTAAT GTTAATGGAA   1513

GGAACCCACT GCTTATTGTT GGAATGGATG AATCATCACC ACATCCTATT ATTCAAGTTT   1573

ACAAACATAA AGAGGAAATG TTGCCCTATA AAAACAAATT TTTTGTTTCT AAGAAGGAAC   1633

GTTACGATTA TGAGCAACTT TGGCGGCCGC GAATTC                             1669
```

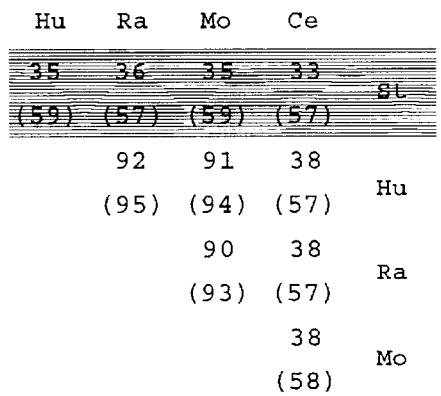

Figure 3A

```
A_Stb-A1    1   MRGNKFCFDLRYLLVVAALAFIYIQMRLFATQSEYVDRLAAAIEAENHCT
B_Ntb-A9    1   MRGNKFCCDFRYLLILAAVAFIYTQMRLFATQSEYADRLAAAIEAENHCT
C_Atb-Full  1   ..MARISCDLRFLLIPAAFMFIYIQMRLFQTQSEYADRLEEAIEEENHCT A_Stb-A1    51  SQTRLLIDKISQQQGRVVALEEQMKEQDQECRQLRALVQDLESKGIKKLI
B_Ntb-A9    51  SQTRLLIDQISQQQGRIVALEEQMKRQDQECRQLRALVQDLESKGIKKLI
C_Atb-Full  49  SQMRGLIDEVSIKQSRIVALEDMKNRQDEELVQLKDLIQTFEKKGIAKLT A_Stb-A1    101 GEVQMPVAAVVVMACSRFDYLERTIKSILKYQTSVASKYPLFISQDGSNP
B_Ntb-A9    101 GNVQMPVAAVVVMACNRADYLEETIKSILKYQISVASKYPLFISQDGSHP
C_Atb-Full  99  QGGQMPVAAVVVMACSRADYLERTVKSVLTYQTPVASKYPLFISQDGSIQ A_Stb-A1    151 DVRKLALSYGQLTYMQHLDFEPVHTERPGELTAYYKIARHYKWALDQLFH
B_Ntb-A9    151 DVRKLALSYEQLTYMQHLDFEPVHTERPGELTAYYKIARHYKWALDQLFY
C_Atb-Full  149 AVFSKELSYNQLTYMQHLDFEPVVTERPGELTAYYKIARHYKWALDQLFY A_Stb-A1    201 KHNFSRVIILEDDMEIAADFFDYFEAGATLLDRDKSIMAISSWNDNGQEQ
B_Ntb-A9    201 KHNFSRVIILEDDMEIAPDFFDYFEAGATLLDRDKSIMAISSWNDNGQMQ
C_Atb-Full  199 KHKFSRVIILEDDMEIAPDFFDYFEAASIMDRDKTIMAASSWNDNGQEQ A_Stb-A1    251 FVQDPDALYRSDFFPGLGWMLSKSTWSELSPKWPKAYWDDWLRLKENHRG
B_Ntb-A9    251 FVQDPYALYRSDFFPGLGWMLSKSTWDELSPKWPKAYWDDWLRLKENHRG
C_Atb-Full  249 FVHDPYALYRSDFFPGLGWMLKESTWDELSPKWPKAYWDDWLRLKENHEG A_Stb-A1    301 RQFIRPEVCRTYNFGEHGSSLGQFFKQYLEPIKLNDVQVDWKSMDLSYLL
B_Ntb-A9    301 RQFIRPEVCRTYNFGEHGSSLGQFFKQYLEPIKLNDVQVDWKSMDLSYLL
C_Atb-Full  299 RQFIAPEVCRTYNFGEHGSSLGQFFSQYLEPIKLNDVTVDWKAKDLGYLT A_Stb-A1    351 EDNYVKHFGDLVKKAKPIHGADAVLKAFNIDGDVRIQYRDQLDFELIARQ
B_Ntb-A9    351 EDNYVKHFGDLVKKAKPIHGADAVLKAFNIDGDVRIQYRDQLDFEKIARQ
C_Atb-Full  349 EGNYTKYFSGLVRQAEPIQGEDLVLKAQNIKDDDRIRYKDQVEFERIAGE A_Stb-A1    401 FGIFEEWKDGVPRAAYKGIVVFREQTSRRVFLVSPDSLRQLGVEDT
B_Ntb-A9    401 FGIFEEWKDGVPRAAYKGIVVFREQTSRRVFLVGHDSLQQLGIEDT
C_Atb-Full  399 FGIFEEWKDGVPRTAYKGVVVFRIQTERRVFLVGPDSVMQLGIRNE
```

Figure 3B

PLANT GNTI SEQUENCES AND THE USE THEREOF FOR THE PRODUCTION OF PLANTS HAVING REDUCED OR LACKING N-ACETYL GLUCOSAMINYL TRANSFERASE I(GNTI) ACTIVITY

This is a continuation of Patent Cooperation Treaty application PCT/EP98/08001. That PCT application was filed on Dec. 9, 1998 and designated the United States of America and additional countries. That PCT application is hereby incorporated by reference in its entirety.

The present invention relates to plant GnTI sequences, in particular, plant nucleic acid sequences encoding the enzyme N-acetyl glucosaminyl transferase I (GnTI), as well as GntI antisense or sense constructs, deduced therefrom, and their translation products, antibodies directed against said translation products as well as the use of the sequence information for the production of transformed microorganisms and of transgenic plants, including those with reduced or lacking N-acetyl glucosaminyl transferase I activity. Such plants with reduced or lacking N-acetyl glucosaminyl transferase I activity are of great importance for the production of glyco-proteins of specific constitution with respect to their sugar residues.

PRIOR ART

In eukaryotes, glycoproteins are cotranslationally assembled in the endoplasmatic reticulum (ER) (i.e. during import into the ER lumen) by the attachment of initially membrane bound glycans (via dolichol pyrophosphate) to specific asparagine residues in the growing polypeptide chain (N-glycosylation). In higher organisms, sugar units located at the surface of the folded polypeptide chain are subjected to further trimming and modification reactions (ref. 1) in the Golgi cisternae. Initially, typical basic $Glc_3Man_9GlcNAc_2$ units of the high-mannose type are formed by means of different glycosidases and glycosyl transferases in the ER, which during the passage through the different Golgi cisternae are subsequently converted to so-called complex glycans. The latter are characterized by less mannose units and the presence of additional sugar residues, such as fucose, galactose and/or xylose in plants and sialic acid (N-acetyl neuraminic acid, NeuNAc) in mammals (ref. 1,2,3). The extent of the modifications can differ between glycoproteins. Single polypetide chains may carry heterogeneous sugar chains. Furthermore, the glycosylation pattern may vary for a specific polypeptide (tissue specific differences), and does not always have to be uniform with respect to a specific glycosylation site, which is referred to as microheterogeneity (ref. 4,5). Up to now, the role of asparagine bound glycans is barely understood, which i.a. results from the fact, that said glycans may serve several functions (ref. 6). However, it can be assumed, that e.g. protection of a polypeptide chain from proteolytic degradation can also be achieved by glycans of a more simple oligomannosyl type (ref.7).

DESCRIPTION OF PROBLEMS

Glycoproteins are highly important in medicine and research. However, large scale isolation of glycoproteins is time-consuming and expensive. The direct use of glycoproteins isolated conventionally often raises problems, since upon administration as a therapeutic, single residues of the glycan components may cause undesired side effects. In this context, the glycan component predominantly contributes to the physico-chemical properties (such as folding, stability and solubility) of the glycoproteins. Furthermore, isolated glycoproteins, as already mentioned above, rarely carry uniform sugar residues, which is referred to as microheterogeneity.

For the production of glycoproteins for medicine and research, yeasts prove to be unsuitable, since they are only able to perform glycosylations of the so-called high-mannose type. While insects and higher plants exhibit complex glycoprotein modifications, these, however, differ from those of animals. Therefore, glycoproteins isolated from plants have a strong antigenic effect in mammals. In most cases, animal organisms with glycosylation defects are not viable, since terminal glycan residues (e.g. of membraneous glycoproteins) mostly possess biological signal function and are indispensable for cell-cell-recognition during the course of embryogenesis. Mammalian cell lines with defined glycosylation defects already exist, the cultivation of which, however, is labour-intensive and expensive.

For mammals, different glycosylation mutants have been described in detail at the cell culture level (ref. 7,8,9,10). Said mutants are either defective in biosynthesis of mature oligosaccharide chains attached to dolichol pyrophosphate or in glycan processing or show alterations in their terminal sugar residues, respectively. Some of these cell lines exhibit a conditional-lethal phenotype or are defective in intracellular protein transport. The consequences of said defects for the intact organism are difficult to estimate. It has been observed, that a modification in the pattern of complex glycans on the cell surfaces of mammals is accompanied by the formation of tumours and metastases, although a functional relationship could not yet unambiguously be demonstrated (ref. 9). Therefore, in mammals glycosylation mutants are very rare. These defects, summarized under HEMPAS (Hereditary Erythroblastic Multinuclearity with a Positive Acidified Serum lysis test) (ref. 10,11), are based either on a deficiency in mannosidase II and/or low levels of the enzyme N-acetyl glucosaminyl transferase II (GnTII), and have strongly limiting effects on the viability of the mutated organism. GntI knock-out mice, in which the gene for GnTI has been destroyed, already die in utero of multiple developmental defects (personal communication, H. Schachter, Toronto).

Until recently, no comparable mutants were known for plants. By the use of an antiserum, which specifically recognizes complex modified glycan chains of plant glycoproteins and which predominantly is directed against the highly antigenic β1→2 linked xylose residues (ref. 12), the applicant was able to isolate several independant mutants from an EMS mutagenized F2 population of the genetic model plant *Arabidopsis thaliana*, which no longer showed complex glycoprotein modification (complex glycan, cgl mutants). After at least five back-crosses, each followed by intermittent selfings (to screen for the recessive defects), the glycoproteins were analyzed. These glycoproteins mainly carried glycans of the $Man_5GlcNAc_2$ type, indicating a defect in N-acetyl glucosaminyl transferase I (GnTI) (ref. 8). Indeed, the Arabidopsis cgl mutants lacked GnTI activity (ref. 13), which normally catalyzes the first reaction in the synthetic pathway to complex modified sugar chains (ref. 1). However, according to observations so far, the viability of the mutated plants is not affected. In recent publications, plants are suggested as a putative source for the production of pharmaceutically relevant glycoproteins or vaccines (ref. 14,15). There however, it was overlooked, that glycoproteins isolated from plants may cause severe immune reactions in mammals, which up to now obstructed the production of heterologous glycoproteins in cultivated plants.

The applicant could demonstrate by way of example for the Arabidopsis cgl mutant, that plants can manage without complex modified glycoproteins to a great extent (ref. 13). Initially, secretory proteins are normally glycosylated in the ER of the mutant. In the Golgi apparatus of the cgl mutant, however, the oligomannosyl chains linked to the polypetide backbone via asparagine residues (N-glycosylation) then remain at the stage of $Man_5GlcNAc_2$ residues, since N-acetyl glucosaminyl transferase I (GnTI) activity is missing (FIG. 1). By this bio-synthesis block, the plant specific complex glycoprotein modification and in particular the attachment of $\alpha 1 \rightarrow 3$ fucose and $\beta 1 \rightarrow 2$ xylose residues is prevented, whereby the strong antigenic effect on the mammalian organism is absent. However, Arabidopsis as a herb only has little utilizable biomass. Therefore, for the large scale production of biotechnologically relevant glycoproteins these cgl plants are less suitable. As an alternative, cultivars, especially Solanaceae, such as potato, tobacco, tomato or pepper and furthermore alfalfa, canola, beets, soybean, lettuce, corn, rice and grain, with missing or highly reduced GnTI activity, would be ideal for the production of heterologous glycoproteins in plants. For this purpose, the methods of homology-dependent gene silencing would be applicable (ref. 16, 17).

As FIG. 3 demonstrates, the homology of the first determined plant GntI sequence from potato (*Solanum tuberosum* L., St) is extraordinary low in comparison to the corresponding known sequences of animal organisms (only 30–40% identity at the protein level, cf. FIG. 3A). Therefore, by the use of heterologous GntI gene sequences an efficient reduction of endogenous complex glycoprotein modification in plants by means of antisense or sense suppression, respectively, (ref. 21), probably cannot be achieved.

Thus, in medicine and research there is still the need for a cost-effective production in suitable organisms of recombinant glycoproteins with a minimum of uniform, i.e. defined sugar residues.

Nature of the present invention:

Since the applicant for the first time has been able to isolate and elucidate plant GntI cDNA sequences, it is now possible i.a. to obtain and, in particular, to generate any plant having reduced or missing GnTI activity, and to detect the corresponding mutants, respectively, by means of reverse genetic approaches following transposon (ref. 18) or T-DNA insertion (ref. 19), respectively, so as to produce glycoproteins with low antigenic potential in said mutants.

i) Enzymes

Generally, the present invention comprises different N-acetyl glucosaminyl transferase I enzymes (EC 2.4.1.101) from plants, e.g. potato (*Solanum tuberosum* L.), tobacco (*Nicotiana tabacum* L.) and *Arabidopsis thaliana* (L.). In particular, the present invention relates to enzymes, which exhibit or contain the amino acid sequences given in FIG. 2 and 3B as well as in the accompanying sequence protocol.

Further, the invention comprises enzymes, which are derived from amino acid sequences of the above mentioned enzymes by amino acid substitution, deletion, insertion, modification or by C-terminal and/or N-terminal truncation and/or extension, and which—if showing enzymatic activity—exhibit a specificity comparable to that of the starting enzyme, i.e. N-acetyl glucosaminyl transferase I activity, and optionally a comparable activity.

In the present context, by the term "comparable activity" an activity is understood, which is in the range of up to 100% above or below that of the starting enzyme. Accordingly, also comprised by the invention are derived enzymes or proteins with very low or completely lacking enzymatic activity, which is detectable by means of one or more of the tests mentioned as follows. The enzyme activity is determined by a standard assay, which is performed with microsomal fractions either under radioactive conditions, e.g. using UDP-[6-$^3$H]GlcNAc as a substrate (ref. 13) or non-radioactive conditions (HPLC method; ref 20). Plant GnTI activity can be detected on the subcellular level in Golgi fractions (ref. 21). On account of low yields, however, it is almost impossible to enrich the enzyme from plants.

Alternatively, an enzyme derived according to the present invention, may optionally be defined as an enzyme, for which a DNA sequence encoding the enzyme can be determined or derived, which hybridizes to a DNA sequence encoding the starting enzyme or to a complementary sequence under stringent conditions, as defined as follows.

For example, an enzyme derived in such a manner represents an isoform, which comprises the amino acids 74 to 446 of the amino acid sequence illustrated in FIG. 2 and in SEQ ID No:1 and 2. This isoform i.a. lacks the membrane anchor formed by amino acids 10 to 29. As a result, this enzyme isoform may be located in the plant cytosol.

As examples for C- and/or N-terminally extended proteins, fusion proteins can be mentioned, comprising in addition to an amino acid sequence according to the invention a further protein, which e.g. exhibits a different enzymatic activity or which may be easily detected in another manner, such as by means of fluorescence or phosphorescence or on account of a reactivity with specific antibodies or by binding to suitable affinity matrices.

Furthermore, the invention comprises fragments of said enzymes, which optionally no longer exhibit any enzymatic activity. Generally, these fragments show an antigenic effect in a host immunized with said fragments, and may accordingly be employed as an antigen for the production of monoclonal or polyclonal antibodies by immunization of a host with those fragments.

Moreover, this invention also relates to N-acetyl glucosaminyl transferase I enzymes from other varieties and plant species, which are obtainable on account of hybridization of their genes or one or more regions of their genes:

to one or more of the DNA sequences and/or DNA fragments of the present invention, as discussed below and/or to suitable hybridization probes according to the invention, which may be prepared on the basis of the amino acid sequences mentioned in the sequence protocol considering the degeneration of the genetic code.

Further comprised by the invention in accordance with the above are enzymes or proteins derived from these N-acetyl glucosaminyl transferase I enzymes, including fusion proteins thereof, as well as fragments of all of these enzymes or proteins.

ii) Antibodies

Another aspect of the present invention relates to the use of the amino acid sequences mentioned above and of fragments thereof having antigenic effects, respectively, for the production of monoclonal or polyclonal antibodies or antisera by immunizing hosts with said amino acid sequences or fragments, respectively, as well as of antibodies or antisera, respectively, per se, which specifically recognize and bind to the enzymes and/or antigens described above. The general procedure and the corresponding techniques for the generation of polyclonal and monoclonal antibodies are all well-known to the persons skilled in the art.

Exemplarily, by the use of a fragment of the GntI cDNA (nucleotides 275 to 1395) represented in FIG. 2 and SEQ ID NO: 1, the recombinant GnTI protein from *Solanum tubero*-

*sum* with 10 N-terminal histidine residues (His-tag) was overexpressed in *E. coli,* and, following affinity purification via a metal-chelate matrix, was employed as an antigen for the production of polyclonal antisera in rabbits (cf. Examples 5 and 6).

One possible use of the antibodies of the invention resides in the screening of plants for the presence of N-acetyl glucosaminyl transferase I.

Binding of the antibody according to the present invention to plant protein(s) indicates the presence of N-acetyl glucosaminyl transferase I enzyme detectable with said antibody. In general, this antibody may then be covalently bound to a carrier in a later step, and optionally be employed for the enrichment or purification of the enzyme by means of column chromatography.

On the other hand, a negative binding result using the antibody of the present invention, i.e. lack of binding to the plant proteins, may suggest, that N-acetyl glucosaminyl transferase I enzyme is absent (or highly modified by mutation), and thus, that N-acetyl glucosaminyl transferase I activity of a plant investigated is missing or highly reduced.

Techniques for the realization of the screening assays mentioned above or the enrichment or purification of enzymes by the use of antibody columns or other affinity matrices (cf. Examples 5 and 6) are well-known to those skilled in the art.

iii) DNA sequences

The present invention further comprises DNA sequences encoding the amino acid sequences of the invention, including amino acid sequences derived therefrom according to the above provisions. In particular, the invention relates to the respective gene, which is the basis of the amino acid sequences described in the FIGS. 2 and 3B and the sequence protocol, and especially, to the cDNA sequences described in FIG. 2 and the sequence protocol, as well as to DNA sequences derived from these genes and DNA sequences.

By the term "derived DNA sequences" are meant sequences, which are obtained by substitution, deletion and/or insertion of one or more and/or smaller groups of nucleotides of the sequences mentioned above and/or by truncation or extension at the 5' and/or 3' terminus. Modifications within the DNA sequence may lead to derived DNA sequences, which encode amino acid sequences being identical to the amino acid sequence encoded by the starting DNA sequence, or to such sequences, in which, compared to the amino acid sequence, which is encoded by the starting DNA sequence, single or a few amino acids are altered, i.e. substituted, deleted and/or inserted, as well as to such sequences, which—optionally in addition—are truncated and/or extended at the C-terminus and/or N-terminus.

Furthermore, the present invention also extends to the complementary sequences of the genes and DNA sequences according to the invention, as well as the RNA transcription products thereof.

Particularly comprised by the present invention are all sequences derived according to the above provisions, which over their entire length or only with one or more partial regions hybridize under stringent conditions to the starting sequences mentioned above or to the sequences complementary thereto or to parts thereof, as well as DNA sequences comprising such sequences.

By the term "hybridization under stringent conditions" in the sense of the present invention is understood a hybridization procedure according to one or more of the methods described below. Hybridizing: up to 20 h in PEG buffer according to Church and Gilbert (0.25 M $Na_2HPO_4$, 1M EDTA, 1% (w/v) BSA, 7% (w/v) SDS, pH 7.5 with phosphoric acid; ref. 22) at 42° C. or in standard hybridization buffers with formamide at 42° C. or without formamide at 68° C. (ref. 23). Washing: 3 times at 65° C. for 30 min in 3×SSC buffer (ref. 23), 0.1% SDS.

In the sense of the present application, the term "hybridization" always means hybridization under stringent conditions, as mentioned above, even if this is not explicitely indicated in the individual case.

Moreover, the invention relates to fragments of the DNA sequences mentioned above, including the DNA sequences derived in accordance with the above provisions, to fragments derived from such fragments by nucleic acid substitution, insertion and/or deletion as well as the corresponding fragments with sequences complementary thereto. Such fragments are i.a. suitable as sequencing or PCR primers, screening probes and/or for uses as discussed below. For the use as a screening or hybridizing probe, the DNA fragments according to the present invention are frequently employed as radio-labelled fragments. Fragments carrying sequences, which are derived from the starting sequences defined above by substitution, deletion and/or insertion of one or more nucleotides, and the sequences complementary thereto, respectively, are comprised by the invention to that extent, as said fragments hybridize under the above mentioned stringent conditions to the starting sequences, or to the sequences complementary thereto, respectively.

On the basis of the DNA sequences mentioned in the sequence protocol and in FIG. 2, DNA fragments according to the invention may for example be obtained starting from plant DNA by means of restriction endonucleases using appropriate restriction sites or by employment of PCR by means of primers appropriately synthesized, or may, as an alternative, also be chemically synthesized. Such techniques are well-known to those skilled in the art.

Moreover, the invention relates to any DNA sequences, which represent a gene or are a part of a gene encoding the enzyme N-acetyl glucosaminyl transferase I and, which in their entirety or in a partial region thereof hybridize under stringent conditions to one or more of the DNA sequences of the invention and/or to one or more of the DNA fragments of the invention and/or to a DNA sequence, which is derived from the amino acid sequences mentioned in the sequence protocol considering the degeneration of the genetic code.

For this purpose, hybridization or screening probes are used as DNA fragments, which generally comprise at least 15 nucleotides, typically between 15 and 30 nucleotides, and, if necessary, substantially more nucleotides. As an example, the primers employed in Example 1 may be used. Alternatively, DNA sequences of appropriate length, derived from the DNA sequences mentioned in the sequence protocol, may be used. As a third possibility, appropriate hybridization probes according to the invention may be developed starting from the amino acid sequences mentioned in the sequence protocol considering the degeneration of the genetic code.

In this respect, a subject-matter of the present invention are also genes encoding N-acetyl glucosaminyl transferase I, which may be detected from other varieties or plant species on account of the hybridization thereof to above mentioned hybridization probes, as well as DNA sequences, DNA fragments and constructs, which are derived therefrom in accordance with the above provisions.

The isolation of the corresponding gene and sequencing thereof following detection by means of the hybridization probes of the invention are well within the skills of a specialist in this field, and are detailed by way of example with respect to N-acetyl glucosaminyl transferase I from *Solanum tuberosum* and to the corresponding enzymes from *Nicotiana tabacum* and *Arabidopsis thaliana* (partial sequence) in the examples.

Finally, another subject matter of the present invention are antisense sequences with respect to any of the above DNA sequences.

iv) Constructs

Also comprised by the invention are constructs, which may optionally comprise besides additional 5' and/or 3' sequences, e.g. linkers and/or regulatory DNA sequences or other modifications, the DNA sequences of the invention, including the DNA sequences derived as detailed above.

An example for this are hybridization or screening probes, which in addition to a DNA sequence of the invention also comprise a detection agent for the verification of hybridization products, which in this case typically is non-radioactive, e.g. fluorescent or phosphorescent molecules, biotin, biotin derivatives, digoxigenin and digoxigenin derivatives. In this respect, however, radioactive or non-radioactive detection agents may be considered, which may be attached to the DNA sequence according to the present invention e.g. by means of end labelling.

A subject-matter of the invention are also antisense and sense constructs with respect to the DNA sequences and fragments according to the present invention, i.e. with respect to the DNA sequences mentioned in the sequence protocol and the corresponding genes;

the DNA sequences derived therefrom in accordance with the above provisions;

one or more regions of these DNA sequences;

DNA sequences, especially from other varieties or plant species, which represent a gene or are a part of a gene, encoding the enzyme N-acetyl glucosaminyl transferase I; and which hybridize under stringent conditions to one or more of the above DNA sequences and/or to one or more of the above DNA fragments and/or to a DNA sequence, which is derived from the amino acid sequences mentioned in the sequence protocol considering the degeneration of the genetic code.

Furthermore, the present invention extends to any DNA-transfer systems such as vectors, plasmids, viral and phage genomes or cosmids, which contain the DNA sequences according to the present invention, e.g. the GntI gene, cDNA and DNA regions according to the invention, as mentioned in the sequence protocol, fragments thereof, in particular antisense or sense constructs and/or cDNA sequences derived therefrom according to the above provisions.

Various techniques for the production or synthesis of DNA, DNA fragments, constructs and transfer systems according to the invention, e.g. digestion by means of restriction endonucleases, PCR amplification using suitable primers, optionally followed by cloning and additional chemical or enzymatic modification starting from plant DNA are well-known to those skilled in the art.

One possibility of application of the DNA hybridization probes according to the invention is the detection of N-acetyl glucosaminyl transferase I genes in plants other than those, from which the DNA sequences mentioned in the sequence protocol were obtained, or the detection of potential (other) isoforms of the N-acetyl glucosaminyl transferase I gene in the starting plants *Solanum tuberosum*, *Nicotiana tabacum* and *Arabidopsis thaliana*.

If it is possible to make use of a plant genomic library or cDNA library for the hybridization experiment, a positive hybridization result of such screening of each library may indicate a clone or a few clones, which contain the desired sequence completely or in part, i.e. the N-acetyl glucosaminyl transferase I gene, combined with only a limited amount of other DNA from the genome of the target plant, which appropriately facilitates cloning and sequencing of the target gene. As an alternative, a PCR amplification of the gene or parts thereof may also be carried out starting from plant DNA and suitable constructs, so-called PCR primers, to facilitate cloning and sequencing.

One use of sequencing primers of the invention, which are synthesized starting from suitable regions of the sequences according to the invention, e.g. enables genomic sequencing starting from the entire target plant genomic DNA cleaved by restriction endonucleases, by means of the Church-Gilbert technique, as well as sequencing at the cDNA level following RT-PCR amplification of the total RNA of the target plant (cf. Expl. 1).

An alternative possibility of application of the DNA hybridization probes according to the present invention derived from the DNA sequences mentioned in the sequence protocol, is the use thereof according to the invention for the detection of plants with reduced or lacking N-acetyl glucosaminyl transferase I activity. The hybridization experiment serves to detect the N-acetyl glucosaminyl transferase I (GntI) gene by which it may be concluded, e.g. owing to a negative hybridization result under stringent conditions, that the GntI gene, and thus, N-acetyl glucosaminyl transferase I activity in a plant investigated is lacking.

Such hybridization techniques for the detection of proteins or genes particularly in plant material by means of DNA probes are also known to the persons skilled in the art. In this context, it is referred to the above statements under item iii) for possible hybridization conditions. Generally, suitable DNA hybridization probes comprise at least 15 nucleotides of a sequence, which for example is derived from the cDNA sequences mentioned in FIG. 2 and the sequence protocol or from the corresponding GntI genes.

v) Transformed microorganisms

Furthermore, the invention relates to microorganisms, such as bacteria, bacteriophages, viruses, unicellular eukaryotic organisms, such as fungi, yeasts, protozoa, algae, and human, animal and plant cells, which have been transformed by one or more of the DNA sequences of the invention or one or more of the constructs of the invention, as illustrated above.

Transformed microorganisms according to the present invention are used e.g. as expression systems for the transforming foreign DNA to obtain the corresponding expression products. For this purpose, typical microorganisms are bacteria, e.g. such as *E. coli*. Furthermore, transformed microorganisms according to the invention, in particular agrobacteria, may be employed e.g. for the transformation of plants by transmission of the transforming foreign DNA.

Methods for the transformation of cells of microorganisms by (foreign) DNA are well-known to those skilled in the art.

For this purpose, e.g. constructs referred to as expression vectors are used, which contain the DNA sequence of the invention under control of a constitutive or inducible promoter, which, if necessary, is additionally tissue specific, so as to enable the expression of the introduced DNA in the target or host cell.

Therefore, a further aspect of the invention is a method for the production of the enzymes and proteins of the invention by using one or more of the transformed microorganisms of the present invention. The method comprises cultivating at least one microorganism transformed by the DNA of the invention, in particular by one of the cDNAs mentioned in the sequence protocol, under the control of an active promoter, as defined above, and isolating the enzyme of the invention from the microorganisms, and, if applicable, also from the culture medium. It is understood, that this method also relates to the production of enzymes and proteins, respectively, which are derived from the enzymes according to the present invention from *Solanum tuberosum, Nicotiana tabacum* and *Arabidopsis thaliana,* as defined under i) above.

Methods for the cultivation of transformed microorganisms are well-known to those skilled in the art. For example, the isolation of the expressed enzyme may be employed according to the method described in Example 5 by means of metal-chelate chromatography or, alternatively, by chromatography via columns, which contain the antibodies against the enzyme bound to the packing material.

vi) Transgenic plants

Furthermore, the invention comprises transgenic plants, which are transformed by means of a DNA sequence according to the invention or a corresponding construct, respectively. Accordingly, there may be obtained e.g. transgenic plants, in which a GnTI deficiency, for example on account of a missing or defectice GntI gene or due to defects in the regulatory regions of this gene, has been removed by complementation using a construct derived from the cDNA sequences mentioned in the sequence protocol, wherein the expression of said construct is under the control of an active constitutive or inducible promoter, which may be additionally tissue specific. In this case, the GnTI enzyme or protein expressed on account of the DNA of the invention contained in the construct and having GnTI activity complements the GnTI activity missing in the starting plant.

Also considered are transgenic plants, in which the GnTI activity already present in the starting plant is increased by additional expression of the GntI transgene introduced by means of a construct according to the present invention. Up to now, the extremely low expression of the GntI gene in vivo accompanied by extremely low enzyme activity, which correspondingly was very difficult to detect, has been a main problem in the investigation of the enzyme N-acetyl glucosaminyl transferase I in plants. The problem of a too low GnTI enzyme activity in plants may be overcome by the coexpression of a DNA according to the present invention.

In this case, it may be preferable for the transformation of plants to employ DNA according to the invention, additionally comprising a sequence region, which following expression enables a facilitated detection and/or enrichment and purification, respectively, of the protein product having GnTI activity. This is for example accomplished by the use of a specific DNA sequence for the expression of a recombinant GnTI enzyme, said sequence carrying a N-terminal or C-terminal sequence extension encoding an affinity marker. If it is additionally intended to provide an amino acid sequence portion between the GnTI enzyme and the affinity marker, which represents a recognition site for a specific protease, cleavage of the N-terminal or C-terminal sequence extension from the GnTI enzyme may be achieved by the subsequent use of this specific protease, and the GnTI enzyme thereby obtained in isolated form.

An example for this is the use of a DNA sequence according to the present invention, which codes for the recombinant GnTI enzyme with a C-terminal sequence extension, encoding the affinity marker AWRHPQFGG (strep-tag; ref. 39), and an intervening protease recognition site IEGR. The expression of the DNA according to the present invention provides GnTI enzymes with the C-terminal sequence extension mentioned, by means of which the expressed protein molecules specifically bind to a streptavidin derivatized matrix, and may thus be isolated. Then, by means of the protease factor Xa specifically recognizing the amino acid sequence IEGR, the GnTI portion of the protein molecules may be released. As an alternative, the complete protein may be removed from the streptavidin derivatized matrix by means of biotin or biotin derivatives.

A further example is represented by DNA sequences of the invention, encoding a protein which comprises multiple, e.g. 10, N-terminally added histidine residues (His-tag) in addition to a GnTI enzyme. Due to the N-terminal histidine residues, isolation or purification, respectively, of the proteins expressed may be easily conducted by metal-chelate affinity chromatography (e.g. Ni sepharose) (cf. also Example 5).

Moreover, the invention comprises portions of such transgenic plants, adequately transformed plant cells, transgenic seeds and transgenic reproduction material.

A further important aspect of the invention is the use of the sequence information discussed above for the production of plants having reduced or lacking N-acetyl glucosaminyl transferase I activity.

The possibilities of identifying plants with reduced or lacking N-acetyl glucosaminyl transferase I activity due to a gene defect or a missing gene by means of antibodies of the invention or screening or hybridization probes of the invention have already been described above.

Two additional possibilities reside in the use according to the invention of antisense or sense constructs, respectively, which are derived from the DNA sequence of a plant GntI gene, for the production of transgenic plants with reduced or lacking N-acetyl glucosaminyl transferase I activity by means of homology-dependent gene silencing (cf. ref. 16,17). The DNA sequence used as a starting sequence for the generation of the constructs, may be derived from the starting plant to be transformed itself but also from a different plant variety or species. In particular, antisense or sense constructs as discussed under items iii) and iv) above are of use. Generally, the constructs employed comprise at least 50 to 200 and more base pairs.

In particular, the constructs employed for this purpose comprise at least 50 to 200 and more base pairs, with a sequence, which is derived on the basis of the cDNA sequences mentioned in the sequence protocol and/or the corresponding GntI genes and/or the derived DNA sequences discussed above and/or DNA fragments according to the present invention and/or the DNA sequences, in particular from other varieties and plant species, which encode N-acetyl glucosaminyl transferase I and which may be identified due to a hybridization under stringent conditions to hybridization or screening probes, as defined under items iii) and iv) above.

Generally, the constructs contain a strong constitutive or inducible promoter, which additionally may be tissue specific, by means of which the antisense or sense DNA sequence regions are controlled.

In the production of transgenic plants by integration of antisense construct(s) into the plant genome or by viral infection of starting plants or plant cells by means of virus containing antisense construct(s) for an extrachomosomal propagation and transcription of the antisense construct or the antisense constructs in infected plant tissue, it is intended to achieve a hybridization of GntI-gene transcripts to transcripts of the antisense DNA region at the RNA level, which prevents translation of the GntI mRNA. The result is a transgenic plant with strongly decreased contents of N-acetyl glucosaminyl transferase I, and thus, a strongly decreased corresponding enzyme activity.

For the transformation of plants according to the invention with antisense constructs, for example constructs may be employed, which hybridize to one of the complete cDNAs, mentioned in FIG. 2 and in the sequence protocol, or to corresponding regions thereof, generally comprising at least 50 to more than 200 base pairs. Moreover, particularly preferred is the use of fragments, the transcripts of which additionally cause a hybridization to a portion of the 5' untranslated region of the GntI mRNA, at which or in the proximity of which usually the attachment of ribosomes would occur. Examples of such constructs are shown in FIG. 4.

In view of the occurence of an isoform in *Solanum tuberosum*, which probably is located in the cytoplasm due to lack of the membrane anchor (aa 10 to 29) of yet unkown function, it may be desirable to target only the N-acetyl glucosaminyl transferase I enzyme located in the Golgi cisternae, i.e. only that enzyme comprising the membrane anchor. One reason for this desire may be the effort or, in the individual case, also the requirement, to affect as little as possible the cytoplasmatic metabolism of the plant cell, for which the cytoplasmatic N-acetyl glucosaminyl transferase I possibly is of importance. For this purpose, antisense constructs may be used according to the present invention, which themselves or the transcripts of which, respectively, hybridize to a DNA or RNA region of the GntI gene or the GntI mRNA, comprising a part of the 5' untranslated region and the coding region including the membrane anchor. Generally, the extension of the region of hybridization up to position 266 of the cDNA in FIG. 2 and SEQ ID NO: 1 is considered harmless for the purpose mentioned above.

In the production of transgenic plants by integration of sense constructs into the plant genome or by viral infection of starting plants or plant cells by means of virus containing sense construct(s) for extrachromosomal propagation and expression of the construct or constructs in infected plant tissue, there are assumed hybridization phenomena in tobacco according to the work of Faske et al. (ref. 17), of said constructs to the endogenous GntI gene at a posttranscriptional or DNA level, respectively, which finally affect or prevent the translation of the GntI gene. Also in this case, the result are transgenic plants having reduced or even lacking N-acetyl glucosaminyl transferase I activity.

Methods for the stable integration of such antisense and sense constructs into the genome of plants, or for the viral infection of plants or plant cells, respectively, for an extrachromosomal propagation and transcription/expression of such constructs in infected plant tissue are well known to those skilled in the art. This includes the direct DNA transfer (e.g. into protoplasts by means of electroporation or by the addition of a high molecular osmotic agent as well as biolistic methods, by which DNA coated particles are shot into the plant tissue), such as the use of natural host/vector systems (e.g. agrobacteria or plant viruses). For viral infection of starting plants or plant cells by viruses containing appropriate constructs for extrachromosomal propagation and transcription/expression of the constructs in infected plant tissue, a variety of specific viruses, such as tobacco mosaic virus (TMV) or potato virus X, is available.

Representative plants, which are suitable for such integration, comprise dicotyledonous as well as monocotyledonous cultivated plants, in particular Solanaceae such as potato, tobacco, tomato and pepper. Additionally, banana, alfalfa, canola, beets, soybean, lettuce, corn, rice and grain, would be suitable target plants for the use of homologous antisense constructs. For example, the sequence from *Arabidopsis thaliana* mentioned in the sequence protocol appears to be particularly suitable as a starting sequence for the transformation according to the invention of Brassicaceae, such as canola plants, by means of sense or antisense constructs. Further plants of interest are any plants, which express glycoproteins of interest for medicine and research.

Generally, it should be noted, that the transformation according to the invention of plants, which in the corresponding region of the GntI gene exhibit a homology of ≧70% at the nucleotide level to the employed antisense or sense constructs according to the present invention, typically results in transgenic plants of the invention, which show the desired reduction of N-acetyl glucosaminyl transferase I activity.

Further, another possibility is seen in the targeted destruction (knock-out) of the N-acetyl glucosaminyl transferase I gene via gene targeting by means of homologous recombination (ref. 24) in a target plant using a suitable DNA fragment derived from the cDNA sequence of the present invention, similar to the procedure established for yeast systems and mammals.

Further, the present invention comprises transgenic plants, which have been transformed by the antisense or sense constructs mentioned above or the viruses containing the same, respectively, as well as parts of such transgenic plants, correspondingly transformed plant cells, transgenic seeds and transgenic reproduction material.

Methods of the production of transgenic plants, e.g. by means of agrobacteria- or virus-mediated as well as direct DNA transfer are known to those skilled in the art. Concerning representative plants for such a transformation, the above mentioned applies.

The plants of the invention and the plants obtained according to the invention, respectively, with reduced or lacking N-acetyl glucosaminyl transferase I activity, may be used according to the invention for the production of glycoproteins with minimal and uniform, i.e. defined, sugar residues. As discussed above, such glycoproteins are of great importance for medicine and research. As a reasonable source of raw material and food as well as due to their unproblematical disposal via composting, plants per se represent ideal bioreactors. According to the present invention, it is now possible to express biotechnologically or pharmaceutically relevant glycoproteins (e.g. therapeutics of low antigenic potential for mammals) in cultivated plants, in which GnTI activity is highly reduced or completely absent.

Accordingly, the invention also comprises a method for the production of glycoproteins with minimal uniform and defined sugar residues, comprising cultivating a transgenic plant according to the invention, of parts of such plants or of plant cells transformed according to the invention, each expressing the desired glycoprotein, as well as isolating the desired glycoprotein from the cultivated material.

In this context, representative cultivated plants are Solanaceae, in particular potato, tobacco, tomato and pepper. Furthermore possible are banana, alfalfa, canola, beets, soybean, lettuce, corn, rice and grain.

The sequence of the enzymatically controlled and plant specific N-glycan modifications, which secretory glycoproteins are subjected to during passage through the Golgi apparatus of higher plants, is schematically shown in FIG. 1.

The biosynthesis block due to lacking or insufficient N-acetyl glucosaminyl transferase I (GlcNAc transferase I) activity in a plant leads, instead of complex glycans, to the predominant formation of glycans of the $Man_5GlcNAc_2$ type, i.e. glycoproteins with uniform and well-defined sugar residues, which are of extremely high importance for medicine and research.

For this purpose, the genes encoding the desired glycoproteins may be expressed in their natural producing plants, which have been transformed according to the present invention e.g. by means of antisense or sense constructs to yield transgenic plants with reduced or missing N-acetyl glucosaminyl transferase I activity.

There is also the possibility to use transgenic plants of the invention displaying reduced or lacking N-acetyl glucosaminyl transferase I activity, which additionally have been transformed by the gene encoding the desired glycoprotein. In order to achieve this, constructs may be employed, which contain the gene encoding the desired glycoprotein under the control of a strong constitutive or inducible promoter, which is optionally tissue specific as well, and lead to the integration of the gene into the plant genome. Alternatively, the transformation may also be conducted by viral infection by means of a virus containing the gene for the desired glycoprotein for extrachromosomal propagation and expression of the gene. The glycoprotein may then be expressed in the respective host plant and obtained therefrom.

Naturally, as an alternative, the procedure may be such, that initially a transformation using an expression construct or virus containing the DNA encoding the glycoprotein is performed, and subsequently, another transformation with one or more of the antisense or sense constructs of the invention or with one or more viruses, containing the corresponding DNA, is performed. It is also possible to perform a simultaneous transformation using both constructs or using one virus containing the antisense or sense construct as well as the gene encoding the desired glycoprotein (piggyback version).

Within the scope of the present invention, there is also considered a viral overinfection of the transgenic plants according to the invention, in which integration of an antisense/sense construct and/or the gene encoding the desired glycoprotein into the genome has already occured, by viruses containing the antisense/sense construct and/or the gene encoding the desired glycoprotein, for an additional extrachromosomal propagation and transcription or expression, respectively, of this DNA. As a result, the concentrations of antisense or sense DNA, respectively, or of the expressed glycoprotein may be increased in the transgenic plant cells.

It may prove to be practical for the production according to the invention of glycoproteins with defined glycosylation, to use tissue specific promoters in such cases, where it is intended to obtain the desired glycoproteins specifically only from certain parts of a plant such as tubers or roots. Today, for a large variety of plant tissues, tissue specific promoters are available, which drive expression of foreign genes specifically only in these tissues. By way of example, tuber specific promoters such as patatin class I (ref. 26) and proteinase inhibitor II promoters (ref. 27) may be mentioned. Under certain conditions, both promoters exhibit expression also in leaf tissue, i.e. they can be induced by high metabolite contents (for example sucrose) and in the case of the proteinase inhibitor II promoter also by mechanical lesion or by spraying with abscisic or jasmonic acid, respectively.

The use of tissue specific promoters may also be indicated in cases, where the DNA sequence or the transcription products or translation products thereof according to the invention, respectively, which are employed for the transformation, turn out to be detrimental to certain plant parts, e.g. due to a negative influence on the metabolism of the corresponding plant cells.

As a representative target glycoprotein, human glucocerebrosidase may be used for the therapy of the hereditary Gaucher's disease (ref. 25). In order to obtain human glucocerebrosidase (GC) with uniform and defined sugar residues, e.g. plants of the present invention which are transformed by means of antisense DNA, may be transformed with the gene encoding human glucocerebrosidase. For this purpose, the human glucocerebrosidase cDNA sequence (ref. 38) is modified at the 3' terminus by means of PCR using gene specific primers in a manner, that the recombinant enzyme carries a C-terminal sequence extension encoding an affinity marker (e.g. AWRHPQFGG, strep-tag; ref. 39) and, optionally, also a protease recognition site (e.g. IEGR) between the GnTI enzyme region and the affinity marker. The GC-cDNA sequence thus altered is expressed in GntI antisense plants of the present invention by using a strong and optionally tissue specific promoter (e.g. for potato under the control of the tuber specific B33 patatin promoter), so that the enzyme synthesized in these plants exclusively carries well defined N-glycans. The affinity marker is intended to facilitate the enrichment of the recombinant enzyme from the transgenic plants. In this case, the expressed protein molecules (GC-strep molecules) bind to a streptavidin derivatized matrix via the affinity marker sequence and can be released therefrom by means of biotin or biotin derivatives. The removal from the strepatavidin derivatized matrix may also be carried out by means of catalytic amounts of a protease, which exhibits a specificity for the protease recognition site located between the GnTI enzyme region and the affinity marker. In this case, only the GnTI enzyme region is released from the matrix. This could be advantageous especially in that case, if the affinity marker sequence has a detrimental effect on the GnTI activity.

Due to their terminal mannose residues, the $Man_5GlcNAc_2$-glycans of the glucocerebrosidase obtained from the plants of the present invention will be recognized by macrophages as an uptake signal, and can thus directly be employed for the therapy of hereditary Gaucher's disease. Currently, a therapy is only possible upon expensive isolation and deglycosylation of native glucocerebrosidase (ref. 25).

Accordingly, the production of recombinant glycoproteins may be highly facilitated by the use of plant GntI sequences compared to conventional methods, e.g. the chemical deglycosylation of purified glycoproteins, which is technically demanding (ref. 25), or a difficult and expensive production in GnTI deficient animal cell lines (ref. 7,10).

DESCRIPTION OF THE FIGURES

FIG. 2: Full length cDNA sequence (SEQ ID NO: 1) of a plant GnTI from potato (*Solanum tuberosum* L.) and amino acid sequence deduced therefrom (SEQ ID NO:2). By way of example, the complete cDNA of the membrane anchor containing GntI isoform from potato leaf tissue (A1) is illustrated. The EcoRI/NotI linkers at the 5' and 3' ends of the cDNA are highlighted by bold letters, the binding sites of the degenerate oligonucleotides used for obtaining the RT-PCR probe are underlined. In contrast to already published animal GnTI sequences, the protein sequence derived from the potato cDNA clones contains a potential N-glycosylation site: Asn-X (without Pro)-Ser/Thr, which is indicated by an asterisk. The region of the membrane anchor is highlighted in italics (aa 10 to 29). The start of the isoform (A8), which is potentially located in the cytosol, is indicated by an arrow.

FIG. 3: A, Degree of identity or similarity, respectively, of the amino acid sequence deduced from a complete GntI cDNA sequence from potato (A1) in comparison to other GnTI sequences of animal organisms, which have been selected from data bases. Identical amino acid positions (in %) are printed in bold letters, similar amino acid positions are given in brackets underneath. Meaning of the abbreviations: Hu, human; Ra, rat; Mo, mouse; Ce, *Caenorhabditis elegans* (roundworm); St, *Solanum tuberosum* (potato). B, Comparison of the derived amino acid sequences of different plant GntI-cDNA clones. A__Stb-A1 (SEQ ID NO:2), GnTI from potato leaf; B__Ntb-A9 (SEQ ID NO:4), GnTI from tobacco leaf (A9); C__Atb-Full (SEQ ID NO:6), GnTI from *Arabidopsis thaliana*. Identical aa are highlighted in black, similar aa in light grey.

FIG. 4). A, Coomassie-stained SDS gel from leaf extracts; B, Western-blot analysis (Ref. 13,33) of parallel samples developed with a complex-glycan antiserum (Ref. 12,13). The lanes contain 30 µg each of total protein: cgl(Ara), Arabidopsis cgl mutant (Ref. 13); WT(Desi), wild-type potato; the numerals refer to individual transgenic potato plants; the arrows represent molecular weight standards of 66, 45, 36 and 29 kDa, respectively.

Figure 1:
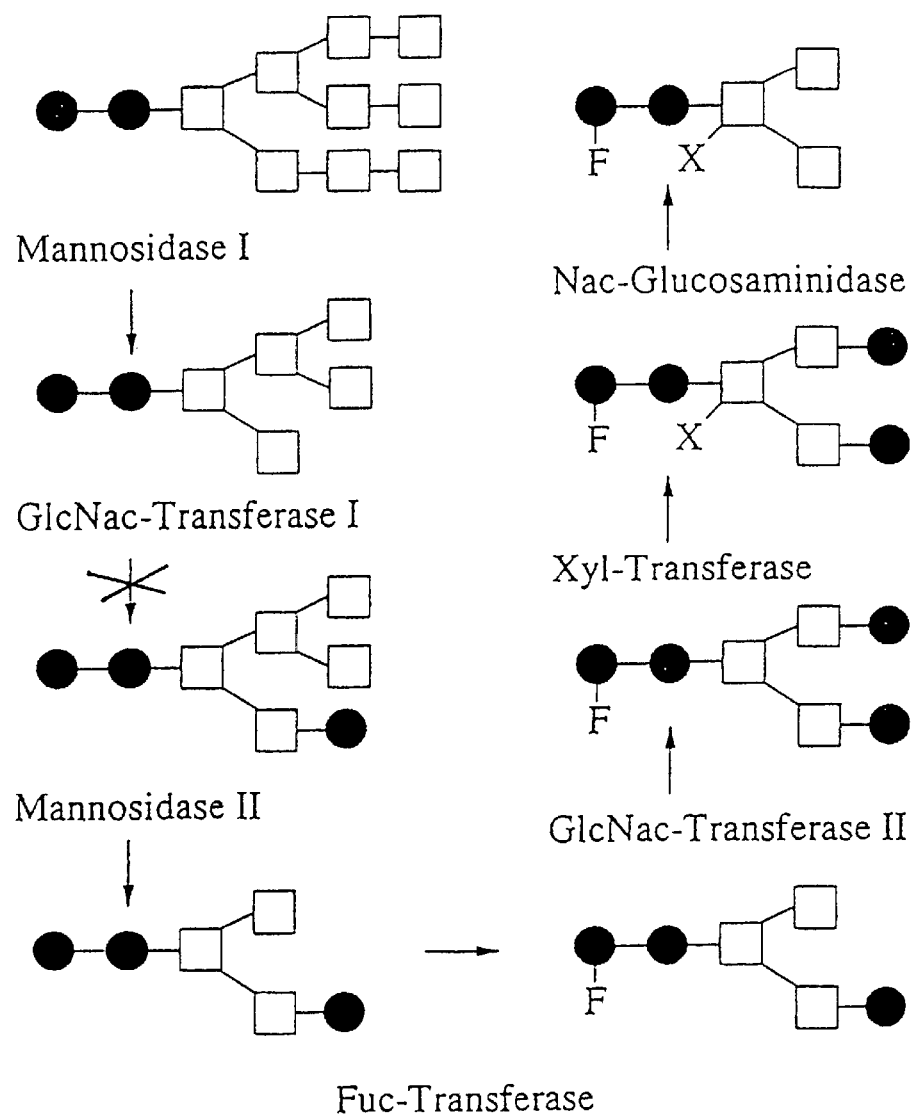
FIG. 1: Sequence of plant specific N-glycan modifications, which secretory glycoproteins are subject to during passage through the Golgi apparatus of higher plants (ref. 28). The biosythesis block to complex modified glycans is based on a deficiency in GnTI activity (which is either caused by a defective or missing GnTI enzyme or by effective reduction of the GntI gene expression) and is indicated by a cross. Meaning of the symbols: (F) fucose residues, (X) xylose residues, (●) GlcNAc residues, (□) mannose residues.

Explanation of the abbreviations used in the text:

Aa, amino acid(s); bp, base pair(s); EMS, Ethyl methane sulfonate (mutagenic agent); F2, second filial generation; Fuc, fucose; Glc, glucose; GlcNAc, N-acetyl glucosamine; GnTI, N-acetyl glucosaminyl transferase I (EC 2.4.1.101); GntI, gene for GnTI (nuclear encoded); kDa, kilodalton; Man, mannose; PCR, polymerase chain reaction; PAGE, polyacrylamide gel electrophoresis; ref., reference; RT-PCR, reverse transcription coupled polymerase chain reaction; SDS, sodium dodecyl sulfate; var., variety; Xyl, xylose.

In the following, the invention will be described in more detail by means of examples, which are only intended to illustrate the invention and shall not limit the invention in any manner.

EXAMPLE 1

Isolation and Characterization of Plant GntI cDNA Clones

Total RNA was isolated from potato and tobacco leaf tissue, and cDNA fragment of about 90 bp were amplified by means of RT-PCR in combination with degenerate primers (procedure analogous to ref. 31), which were derived from conserved amino acid regions of known GnTI sequences from animal organisms (sense primer 1* (SEQ ID NO:7), 5'-TG(CT) G(CT)I (AT) (GC) I GCI TGG (AC)A(CT) GA(CT) AA(CT) -3'; antisense primer 3* (SEQ ID NO:8), 5' -CCA ICC IT(AG) ICC (ACGT)G(CG) (AG)AA (AG)AA (AG)TC-3'; 30 pmol of each primer per 50 µl PCR assay at an annealing temperature of 55° C. and 45 cycles). Following gel elution, the ends of the PCR products were repaired (i.e. blunt ended using DNA polymerase I and phosphorylated using T4 polynucleotide kinase) and clones into the EcoRV restriction site of pBSK (Stratagene). By comparison with known GnTI sequences between the primers (arrows), the identity of the derived amino acid sequences from the potato and tobacco RT-PCR products could be confirmed as being homologous; =Q(R/M)QFVQDP(D/Y)ALYRS (SEQ ID NO:9)– (homologous aa are underlined). Of one clone each, radiolabelled probes were synthesized by means of PCR (standard PCR assay using degenerate primers as above, nucleotide mixture without dCTP, but instead with 50 µCi α-$^{32}$P-dCTP [>3000 Ci/mMol]), and different cDNA libraries were screened for GntI containing clones using the corresponding homologous potato or tobacco probes, respectively (procedure analogous to ref. 31; the stringent hybridization conditions have already been described in the text above). The cDNA libraries were prepared from mRNA of young and still growing plant parts (sink tissues). Following cDNA synthesis and ligating EcoRI/NotI adaptors (cDNAsynthesis kit, Pharmacia) EcoRI compatible lambda arms were ligated, those packaged and used to transfect *E. coli* XL1 Blue cells (Lambda ZAPII cloning and packaging system, Stratagene). Following amplification of the libraries, one full-length GntI clone each was isolated from a potato leaf sink library (A1 according to FIG. 2 and SEQ ID NO: 1) and a tobacco leaf sink library (A9 according to SEQ ID NO: 3), as well as two additional clones from a tuber sink library (A6, A8). The deduced GnTI amino-acid sequences contain a potential N-glycosylation site, Asn-X (without Pro)-SerlThr, in contrast to those of animals. One of the tuber GntI cDNA sequences carries stop condons in all three reading frames in front of the first methionine (A8). The coding region shows high homology to the longer tuber clone (A6) (only 2 aa substitutions), but displays a completely different 5' non-translated region. Furthermore, the membrane anchor characteristic for the Golgi enzyme is missing, so that this GnTI isoform might be located in the cytosol. Sequence comparisons carried out by means of the gap or pileup option, respectively, and the box option of the gcg software package (J. Devereux, P. Haeberli, O. Smithies (1984) Nucl.

Acids Res. 12: 387–395) indicate, that the deduced plant GnTI amino-acid sequences exhibit only 30–40% identity and 57–59% similarity to those of animal organisms (FIG. 3A), while they are highly homologous among each other (75–90% identity, FIG. 3B).

The procedure in the case of *Arabidopsis thaliana* was analogous, wherein for the preparation of a specific probe first a partial GntI sequence was amplified by RT-PCR using GntI sense primer 4A (SEQ ID NO:10; 5'-ATCGGA AAGCTTGGATCC CCA GTG GC(AG) GCT GTA GTT GTT ATG GCT TGC -3'; HindIII restriction site underlined, BamHI printed in bold) and antisense primer 3*, as defined above. First, a 5'-incomplete cDNA clone was isolated from a phage library (Lambda Uni-Zap) using this probe. By means of a vector insert PCR, the missing 5'-terminus was amplified from another library (via a unique SpeI restriction site in the 5' region) and assembled to yield a full-length cDNA sequence. The nucleic acid sequence determined by means of sequencing is listed in SEQ ID NO: 5.

EXAMPLE 2

Functional Complementation of a GnTI Defect Using GntI cDNA Upon Transient Expression in Protoplasts of the *Arabidopsis thaliana* cgl Mutant Approximately 4 weeks subsequent to sowing, protoplasts were isolated from leaves of cgl mutants cultivated under sterile conditions (nonstainer plants following 5 backcrosses, ref. 13), transformed with expression constructs of the complete GntI cDNA sequences (NotI cDNA fragments, cf. FIG. 4) in sense (pA35N-A1s or pA35N-A9s, respectively) or antisense orientation (pA35N-A1as or pA35N-A9as, respectively), and cultivated for 96 h at room temperature in the dark (50 μg of plasmid DNA each per 1 million protoplasts, PEG method according to ref. 32). Subsequent SDS-PAGE of the protoplast extracts and Western-blot analysis (analogous to ref. 13, 33) indicated functional complementation of the GnTI defect, i.e. complex glycosylation of numerous protein bands upon transient expression of the potato A1 and tobacco A9 sense constructs, but not of the corresponding antisense constructs in protoplasts of the Arabidopsis cgl mutant (data not shown).

EXAMPLE 3

Figure 4:
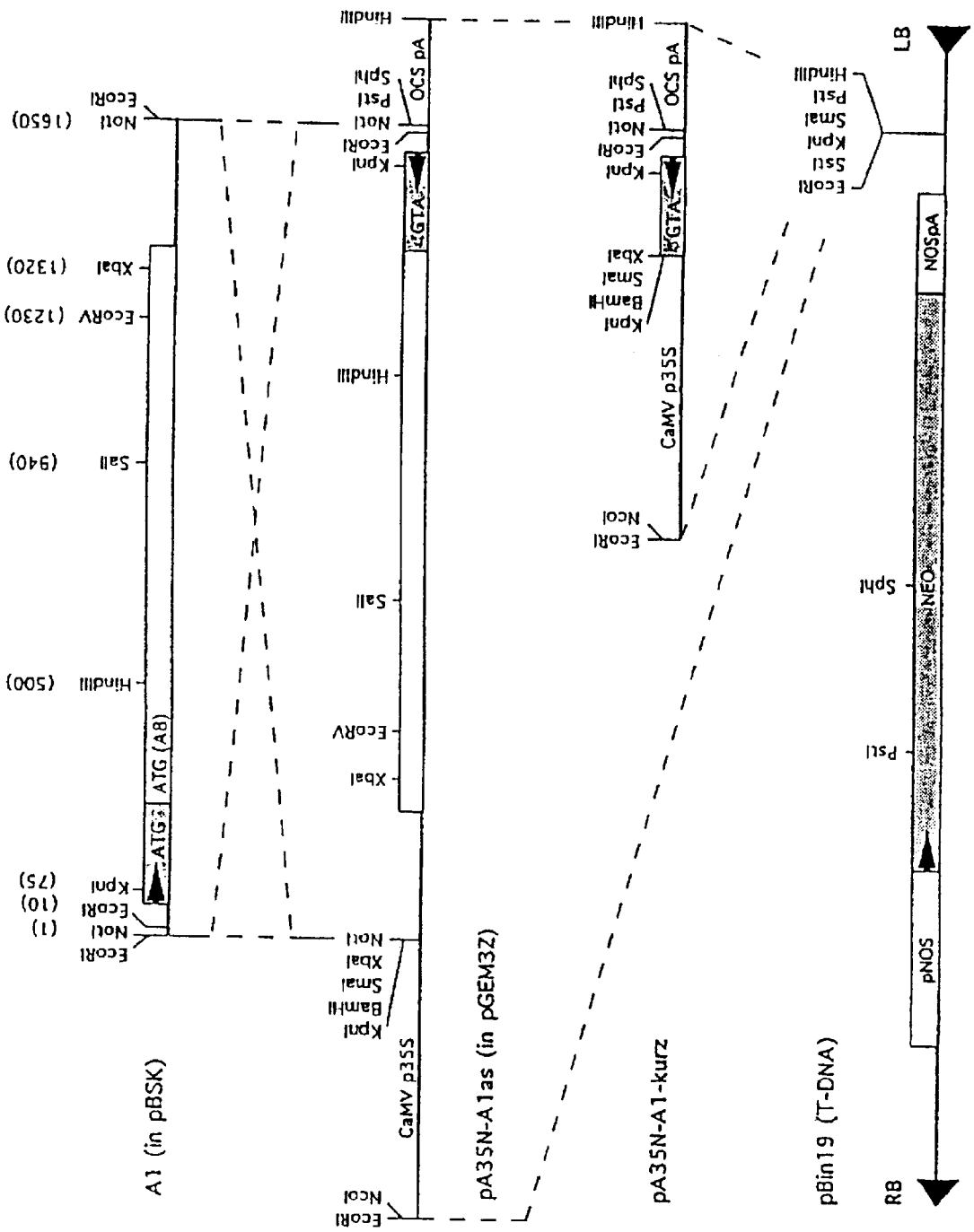
FIG. 4: Cloning strategy of the GntI-antisense constructs used. Following fill-in of the ends, a NotI linker was introduced into the SalI restriction site of the polylinker region of the plant expression vector pA35 (=pA35N) (ref. 29), and the complete Al-GntI-cDNA was inserted into pA35N via NotI. The corresponding antisense construct (=pA35N-Alas) was inserted into binary vector pBin19 (ref. 30) via EcoRI and HindIII. Additionally, following PCR amplification, a 5' fragment of the A1-GntI-cDNA comprising 270 bp was cloned into pA35N via XbaI and NotI restriction sites in antisense orientation (=pA35N-A1-short) and also inserted into pBin19. Abbreviations; Numerals in brackets, positions of the restriction sites in the A1-GntI-cDNA (in base pairs); pBSK, cloning vector (Stratagene): pGEM3Z, cloning vector (Promega); CaMVp35S, constitutive 35S promoter of cauliflower mosaic virus; OCSpA, polyadenylation signal of octopin synthase; pNOS, promoter of nopaline synthase; NEO, neomycin phosphotransferase (selection marker, confers kanamycin resistance); NOSpA, polyadenylation signal of nopaline synthase; LB/RB, left/right border of the T-DNA of the binary vector; arrow, translation initiation (ATG); A8, start of the GnTI isoform, which is potentially located in the cytosol (7 aa substitutions in comparison to A1).

Cloning of the Binary Expression Constructs pBin-35-A1as and pBin-35-A1-short (cf. FIG. 4).

Into the SalI restriction site of the polylinker region (corresponding to the one of pUC18) of plant expression vector pA35 (ref. 29), a NotI linker was introduced subsequently to the fill-in of the ends (=pA35N), and the complete A1-GntI-cDNA (nucleotides 9 to 1657, according to the cDNA in FIG. 2) was inserted into pA35N via NotI (sense construct pA35N-A1s and antisense construct pA35N-A1as, respectively). The expression cassettes of the sense and antisense construct, respectively, were isolated via the terminal restriction sites (filled-in NcoI restriction site, partial post digestion with HindIII) as a fragment of about 2410 bp and inserted into the EcoRI (filled-in) and HindIII restriction sites of the binary vector pBin19 (Ref. 30) (=pBin-35-A1s and pBin-35-A1as, respectively). The EcoRI restriction site of the vector is restored by fusion with the equally filled-in NcoI restriction site of the fragment. By means of a standard PCR assay (sense primer (SEQ ID NO: 11): KS sequencing primer (Stratagene) extended for PCR, 5'-GGC CCC CCC TCG AGG TCG ACG GTA TCG-3'; antisense primer (SEQ ID NO: 12): 5'-GGGCCTCTAGACTCGAG AGC (CT)AC TAC TCT TCC TTG CTG CTG GCT AAT CTT G-3', XbaI restriction site underlined, XhoI restriction site in italics), there was additionally amplified a 5'-fragment of the GntI cDNA at an annealing temperature of 50° C. (nucleotides 9 to 261, according to the cDNA in FIG. 2 and SEQ ID NO: 1). The PCR product was digested with XbaI (within the antisense primer) and NotI (within the 5'-linker of the cDNA), isolated as a fragment of about 260 bp and cloned into pA35N (=pA35N-A1-short). The expression cassette of the short antisense construct was also inserted into pBin19 (=pBin-35-A1-short) as a EcoRI/HindIII fragment (about 1020 bp).

EXAMPLE 4

Figure 5:
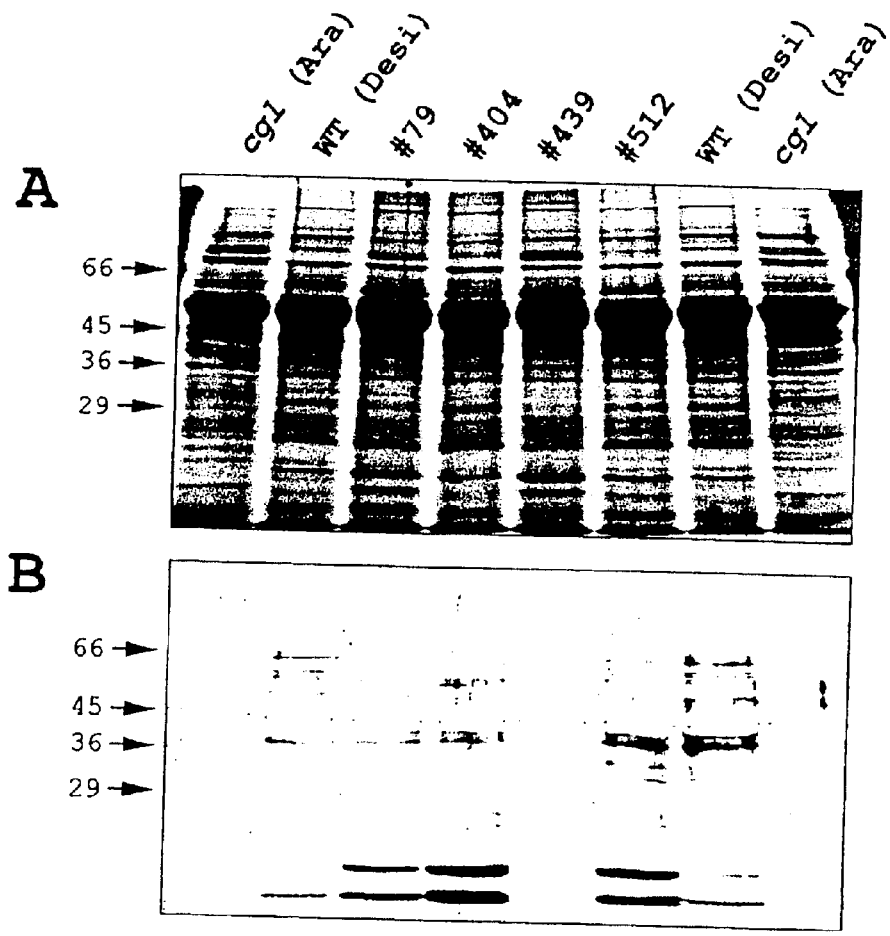
FIG. 5: Extent of suppression of complex glycoprotein modification in transgenic potato plants transformed with the long GntI antisense construct (cf.

Transformation of Agrobacteria by Means of the Binary GntI Constructs and Regeneration of Transgenic Potato and Tobacco Plants, Respectively, from Infected Leaf Discs The binary antisense GntI constructs (pBin-35-A1as and pBin-35-A1-short) were transformed into the Agrobacterium strain GV2260 (ref. 34, 35). By way of example, sterile leaf discs of potato plants var. Désirée and of tobacco plants var. Wisconsin 38 were infected with the recombinant agrobacterial lines (50 μl of a fresh overnight culture in 10 ml liquid 2MS medium: 2% sucrose in Murashige & Skoog salt/vitamin standard medium, pH 5.6; small pieces of leaf without midrip; co-cultivation for 2 days in the dark in phytotrons). Subsequent to washing of the infected leaf pieces in 2MS medium with 250 μg/ml claforan, transgenic plants were regenerated from said pieces in tissue culture, under kanamycin selection (potato protocol ref. 26; tobacco protocol ref. 36) and analyzed for reduced GnTI activity (exemplary shown in FIG. 5 for transgenic potato plants). As apparent from FIG. 5, antisense suppression of complex glycoprotein modifiaction was successful in transgenic potato plant #439. The determined reduction of complex glycoprotein modification was stable in this transformant over the entire investigation period of several months and has been verified in three tests which were performed in an interval of about 1 month each. For the respective transgenic tobacco plants, analogous results were obtained.

EXAMPLE 5

Production of Recombinant Potato GnTI Protein (for the production of Antibodies)

Recombinant GnTI carrying 10 additional N-terminal histidine residues (His-tag) was produced in *E. coli* by means of the pET system (Novagen) and purified by metal-chelate affinity chromatography. A CDNA fragment comprising nucleotides 275–1395 of the potato GntI cDNA (corresp. to aa 75–446, FIG. 2 and SEQ ID NO: 1 and 2, respectively) was amplified by standard PCR (annealing temperature of 50° C., 30 cycles, ref. 31) (sense primer GntI-5' fus (SEQ ID NO: 13): 5'-CATGGATCC CTC GAG AAG CGT CAG GAC CAG GAG TGC CGG C-3'; antisense primer GntI-3' stop (SEQ ID NO: 14): 5'-ATCCCG <u>GGATCCG</u> CTA CGT ATC TTC AAC TCC AAG TTG-3'; XhoI and BamHI restriction sites, respectively, are underlined, stop codon in italics), and inserted into vector pET16b (Novagen) (=pET-His-A1) via the restriction sites of the synthetic primer (5'-XhoI-GntI-BamHI-3'). Following propagation and analysis in *E. coli* XL1-Blue (Stratagene) the construct was stored as a glycerol culture. Competent *E. coli* BL21 (DE3) pLysS cells (Novagen) were transformed with pET-His-A1 for overexpression. Addition of IPTG (Isopropyl-1-thio-β-D-galactopyranoside, at 0.5–2 mM) to a BL21 culture in logarithmic growth phase, initially induces the expression of T7 RNA polymerase (from the bacterial chromosome), and thus, also the expression of the recombinant fusion protein under control of the T7 promoter in pET vectors (Novagen). By means of metal-chelate chromatography using TALON matrix (Clontech), recombinant potato GnTI was purified from induced BL21:pET-His-A1 cells under denaturing conditions via its His-tag (manufacturer's protocol, Novagen), and the preparation was verified with respect to homogeneity by means of SDS-PAGE.

EXAMPLE 6

Raising of Polyclonal Antibodies in Rabbits

Figure 6:
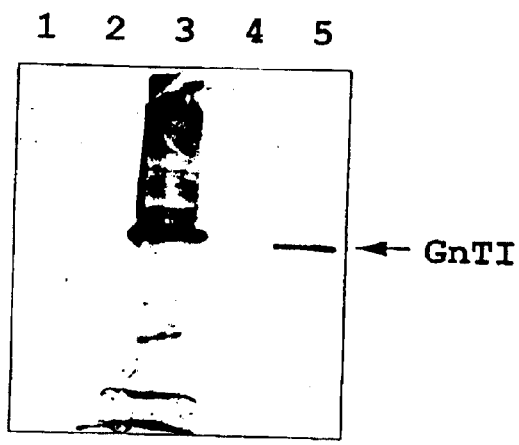
FIG. 6: Detection of specificity of the generated GnTI antiserum following cell fractionation (Ref. 40) of tobacco callus material. For Western-blot analysis (Ref. 13,33) 30 µg of protein were applied per lane. The antiserum was used in 1:1000 dilution. Lane 1, homogenate following separation of cellular debris; lane 2, vesicle fraction following column chromatography; lane 3, sucrose gradient fraction I (microsomes); lane 4, sucrose gradient fraction II (plastids); lane 5, antigen used for immunization (recombinant GnTI fusion protein); arrow, molecular weight of about 49 kDa.

Recombinant potato GnTI (from Expl. 5) was used as an antigen. Following the harvest of some milliliters of preimmune serum, the rabbits were subcutaneously injected with 300–500 μg of affinity-purified protein together with 25 μg of GMDP adjuvant (Gerbu) in intervals of three weeks. Subsequent to three basis injections, the animals were bled from the ear vein 12 to 14 days after the respective successive injection (boost), the serum harvested (ref. 37) and tested for recognition of recombinant GnTI by Western-blot analyses (dilution 1:200 to 1:2000). The antiserum of the boosts resulting in the lowest background-to-signal ratio were mixed with 0.04% sodium azide, aliquoted and kept at +4° C. or for long-term storage at −20° C., respectively. As shown in FIG. 6, Western-blot analyses of tobacco callus cells (BY-2 suspension culture) revealed a specific GnTI signal in enriched microsomal fractions, which indicates, that antibodies raised against the recombinant protein specifially recognize plant GnTI. The detection was carried out with enriched microsomal fractions (ER and Golgi vesicles), since—due to low amounts—it is not possible to detect GnTI protein in crude plant extracts by means of the employed Western-blot method.

REFERENCES

1) R Kornfeld, S Kornfeld (1985) Assembly of asparagine-linked oligosaccharides. Annu Rev Biochem 54: 631–664
2) G P Kaushal, T Szumilo, A D Elbein (1988). Structure and biosynthesis of plant N-linked glycans. In J Preiss (editor) The Biochemistry of Plants, Vol 14: Carbohydrates. Academic Press, San Diego, Calif., pp 421–463
3) L Faye, M J Chrispeels (1989) Apparent inhibition of β-fructosidase secretion by tunicamycin may be explained by breakdown of the unglycosylated protein during secretion. Plant Physiol 89: 845–851
4) T W Rademacher, R B Parekh, R A Dwek (1988) Glycobiology. Annu Rev Biochem 57: 785–838
5) A Sturm (1991) Heterogeneity of the complex N-linked oligosaccharides at specific glycosylation sites of 2 secreted carrot glycoproteins. Eur J Biochem 199: 169–179
6) K Olden, B A Bernard, M J Humphries, T Yeo, S L White, S A Newton, H C Bower, J B Parent (1985) Function of glycoprotein glycans. Trends Biochem Sci 10: 78–82
7) P Stanley (1989) Chinese hamster ovary cell mutants with multiple glycosylation defects for production of glycoproteins with minimal carbohydrate heterogeneity. Mol Cell Biol 9: 377–383
8) R Kumar, J Yang, R D Larsen, P Stanley (1990) Cloning and expression of N-acetylglucosaminyltransferase I, the medial Golgi transferase that initiates complex N-linked carbohydrate formation. Proc Natl Acad Sci USA 87: 9948–9952
9) J W Dennis, S Laferte, C Waghorne, M L Breitman, R S Kerbel (1987) β→6 branching of Asn-linked oligosaccharides is directly associated with metastasis. Science 236: 582–585
10) M N Fukuda (1990) HEMPAS disease: genetic defect of glycosylation. Glycobiology 1: 9–15
11) M N Fukuda, K A Masri, A Dell, L Luzzatto, K W Moremen (1990) Incomplete synthesis of N-glycans in congenital dyserythropoetic anemia type II caused by a defect in the gene encoding α-mannosidase II. Proc Natl Acad Sci USA 87: 7443–7447
12) M Laurière, C Laurière, M J Chrispeels, K D Johnson, A Sturm (1989) Characterization of a xylose-specific antiserum that reacts with the complex asparagine-linked glycans of extracellular and vacuolar glycoproteins. Plant Physiol 90: 1182–1188
13) A von Schaewen, A Sturm, J O'Neill, M J Chrispeels (1993) Isolation of a mutant Arabidopsis plant that lacks N-acetyl glucosaminyl transferase I and is unable to synthesize Golgi-modified complex N-linked glycans. Plant Physiol 102: 1109–1118
14) J K-C Ma, M B Hein (1995) Plant antibodies for immunotherapy. Plant Physiol 109: 341–346
15) A S Moffat (1995) Medical applications: Exploring transgenic plants as a new vaccine source. Science 268: 658–660 (summary of two original publications in the same issue)
16) C B Taylor (1997) Comprehending cosuppression. Plant Cell 9: 1245–1249 (summary of several original publications in the same issue)
17) M Faske, J E Backhausen, M Sendker, M Singer-Bayrle, R Scheibe, A von Schaewen (1997) Transgenic tobacco plants expressing pea chloroplast Nmdh cDNA in sense and antisense orientation: Effects on NADP-MDH level, stability of transformants, and plant growth. Plant Physiol 115: 705–715
18) R Koes, E Souer, A van Houwelingen, L Mur, C Spelt, F Quattrocchio, J Wing, B Oppedijk, S Ahmed, T Maes, T Gerats, P Hoogeveen, M Meesters, D Kloos, JNM Mol (1995) Targeted gene inactivation in petunia by PCR-based selection of transposon insertion mutants. Proc Acad Sci USA 92: 8149–8153
19) E C McKinney, N Ali, A Traut, K A Feldmann, D A Belostotsky, J M McDowell, R B Meagher (1995) Sequence-based identification of T-DNA insertion mutations in Arabidopsis: actin mutants act2-1 and act4-1. Plant J 8: 613–622
20) F Altmann, G Kornfeld, T Dalik, E Staudacher, J Glössl (1993) Processing of asparagine-linked oligosaccharides in insect cells. N-acetylglucosaminyl transferase I and II activities in cultured lepidopteran cells. Glycobiology 3: 619–625
21) A Sturm, K D Johnson, T Szumilo, A D Elbein, M J Chrispeels (1987) Subcellular localization of glycosidases and glycosyltransferases involved in the processing of N-linked oligosaccharides. Plant Physiol 85: 741–745

22) G M Church, W Gilbert (1984) Genomic sequencing. Proc Acad Sci USA 81: 1991–1995
23) J Sambrook, E F Fritsch, T Maniatis (1989) Molecular cloning: a laboratory manual (2nd edn), Cold Spring Harbor Laboratory, Cold Spring Harbor, N.Y.
24) H Puchta, B Hohn (1996) From centiMorgans to base pairs: homologous recombination in plants. Plant Sci 1: 340–348
25) N W Barton, F S Furbish, G J Murray, M Garfield, R O Brady (1990) Therapeutic response to intravenous infusions of glucocerebrosidase in a patient with Gaucher disease. Proc Natl Acad Sci USA 87: 1913–1916
26) M Rocha-Sosa, U Sonnewald, W-B Frommer, M Stratmann, J Schell, L Willmitzer (1989) Both developmental and metabolic signals activate the promoter of a class I patatin gene. EMBO J 8: 23–29
27) T Hildmann, M Ebneth, H Pena-Cortes, J J Sanchez-Serrano, L Willmitzer, S Prat (1992) General roles of abscisic and jasmonic acids in gene activation as a result of mechanical wounding. Plant Cell 4: 1157–1170
28) K D Johnson, M J Chrispeels (1987) Substrate specificities of N-acetylglucosaminyl-, fucosyl-, and xylosyl-transferases that modify glycoproteins in the Golgi apparatus of bean cotyledons. Plant Physiol 84: 1301–1308
29) H Hofte, L Faye, C Dickinson, E M Herman, M J Chrispeels (1991) The protein-body proteins phytohemagglutinin and tonoplast intrinsic protein are targeted to vacuoles in leaves of transgenic tobacco. Planta 184: 431–437
30) M Bevan (1984) Binary Agrobacterium vectors for plant transformation. Nucl Acids Res 12: 8711–8721
31) K Graeve, A von Schaewen, R Scheibe (1994) Purification, characterization and cDNA sequence of glucose-6-phosphate dehydrogenase from potato (*Solanum tuberosum* L.). Plant J 5: 353–361
32) B Damm, R Schmidt, L Willmitzer (1989) Efficient transformation of *Arabidopsis thaliana* using direct gene transfer to protoplasts. Mol Gen Genet 213: 15–20
33) A von Schaewen, M Stitt, R Schmidt, L Willmitzer (1990) Expression of a yeast-derived invertase in the cell wall of tobacco and Arabidopsis plants leads to accumulation of carbohydrate, inhibition of photosynthesis and strongly influences growth and phenotype of transgenic tobacco plants. EMBO J. 9: 3033–3044
34) R Deblaere, B Bytebier, H De Greve, F Debroeck, J Schell, M van Montagu, J Leemans (1985) Efficient octopine Ti plasmid-derived vectors for Agrobacterium mediated gene transfer to plants. Nucl Acids Res 13: 4777–4788
35) R Höfgen, L Willmitzer (1988) Storage of competent cells for Agrobacterium transformation. Nucl Acids Res 16: 9877
36) T Voelker, A Sturm, M J Chrispeels (1987) Differences in expression between two seed lectin alleles obtained from normal and lectin-deficient beans are maintained in transgenic tobacco. EMBO J 6: 3571–3577
37) E Harlow, D Lane (1988) Antibodies: A Laboratory Manual, Cold Spring Harbor Laboratory Press, Cold Spring Harbor, N.Y.
38) J Sorge, C West, B Westwood, E Beutler (1985) Molecular cloning and nucleotide sequence of human cerebrosidase cDNA. Proc Natl Acad Sci USA 82: 7289–7293
39) T G M Schmidt, A Skerra (1993) The random peptide library-assisted engineering of a C-terminal affinity peptide, useful for the detection and purification of a functional Ig Fv fragment. Prot Engineering 6: 109–122
40) M van der Wilden, N R Gilkes, M J Chrispeels (1980) The endoplasmic reticulum of mung bean cotyledons: role in the accumulation of hydrolases in protein bodies during seedling growth. Plant Physiol. 66: 390–394

What is claimed is:

1. An isolated nucleic acid which encodes a polypeptide having N-acetyl glucosaminyl transferase I activity and is selected from the group consisting of:
   a) a nucleic acid comprising SEQ ID NO: 1;
   b) a DNA sequence encoding the amino acid sequence of SEQ ID NO: 2;
   c) and complements thereof.

2. A DNA vector comprising the nucleic acid of claim 1 in the sense or anti-sense orientation.

3. A microorganism transformed with the DNA construct of claim 2.

4. A transgenic plant, transgenic seed, transgenic reproduction material, part of a transgenic plant or transformed plant cell, comprising the DNA vector of claim.

* * * * *

SEQUENCE LISTING

```
<160> NUMBER OF SEQ ID NOS: 14

<210> SEQ ID NO 1
<211> LENGTH: 1669
<212> TYPE: DNA
<213> ORGANISM: Solanum tuberosum
<220> FEATURE:
<221> NAME/KEY: misc_feature
<222> LOCATION: (659)...(667)
<223> OTHER INFORMATION: function: Asn codon in this context is a
      potential glycosylation site;
      product: N-glycosylation consensus sequence;
      phenotype: N-glycans modulate protein properties;
<220> FEATURE:
<221> NAME/KEY: misc_feature
<222> LOCATION: (659)...(667)
<223> OTHER INFORMATION: standard_name: N-glycosylation site;
      label: pot-CHO;
      note: GnTI-coding sequences from animals do not
      contain this feature.
<220> FEATURE:
<221> NAME/KEY: CDS
<222> LOCATION: (53)...(1393)
<223> OTHER INFORMATION: codon_start: 53;
      function: initiates complex N-glycans on secretory
      glycoproteins;
      EC_number: 2.4.1.101;
<220> FEATURE:
<221> NAME/KEY: CDS
<222> LOCATION: (53)...(1393)
<223> OTHER INFORMATION: product: beta-1,2-N-acetylglucosaminyl-
```

```
        transferase I;
        evidence: EXPERIMENTAL;
<220> FEATURE:
<221> NAME/KEY: CDS
<222> LOCATION: (53)...(1393)
<223> OTHER INFORMATION: gene: cgl;
        standard_name: gntI;
        label: ORF;
        note: first gntI sequence from potato (unpublished).
<220> FEATURE:
<221> NAME/KEY: 5'UTR
<222> LOCATION: (15)...(52)
<220> FEATURE:
<221> NAME/KEY: 3'UTR
<222> LOCATION: (1394)...(1655)
<220> FEATURE:
<221> NAME/KEY: CDS
<222> LOCATION: (80)...(139)
<223> OTHER INFORMATION: function: membrane anchor (amino acids 10-29);
        product: hydrophobic amino acid stretch in GnTI;
        standard_name: membrane anchor of a type II Golgi
        protein;
<220> FEATURE:
<221> NAME/KEY: CDS
<222> LOCATION: (80)...(139)
<223> OTHER INFORMATION: note: identified by comparison with GnTI
        sequences from animals.
<220> FEATURE:
<221> NAME/KEY: misc_feature
<222> LOCATION: (1)...(14)
<223> OTHER INFORMATION: function: used for cloning the cDNA library in
        Lambda ZAPII;
        product: EcoRI/NotI-cDNA adapter;
        number: 1.
<220> FEATURE:
<221> NAME/KEY: misc_feature
<222> LOCATION: (1656)...(1669)
<223> OTHER INFORMATION: product: EcoRI/NotI-cDNA adapter;
        number: 2.

<400> SEQUENCE: 1
gaattcgcgg ccgcctgaga aaccctcgaa ttcaatttcg catttggcag ag atg aga          58
                                                            Met Arg
                                                              1 ggg aac aag ttt tgc ttt gat tta cgg tac ctt ctc gtc gtg gct gct          106
Gly Asn Lys Phe Cys Phe Asp Leu Arg Tyr Leu Leu Val Val Ala Ala
        5                  10                  15 ctc gcc ttc atc tac ata cag atg cgg ctt ttc gcg aca cag tca gaa          154
Leu Ala Phe Ile Tyr Ile Gln Met Arg Leu Phe Ala Thr Gln Ser Glu
 20                  25                  30 tat gta gac cgc ctt gct gct gca att gaa gca gaa aat cat tgt aca          202
Tyr Val Asp Arg Leu Ala Ala Ala Ile Glu Ala Glu Asn His Cys Thr
 35                  40                  45                  50 agt cag acc aga ttg ctt att gac aag att agc cag cag caa gga aga          250
Ser Gln Thr Arg Leu Leu Ile Asp Lys Ile Ser Gln Gln Gln Gly Arg
                 55                  60                  65 gta gta gct ctt gaa gaa caa atg aag cat cag gac cag gag tgc cgg          298
Val Val Ala Leu Glu Glu Gln Met Lys His Gln Asp Gln Glu Cys Arg
         70                  75                  80 caa tta agg gct ctt gtt cag gat ctt gaa agt aag ggc ata aaa aag          346
Gln Leu Arg Ala Leu Val Gln Asp Leu Glu Ser Lys Gly Ile Lys Lys
         85                  90                  95 tta atc gga gat gtg cag atg cca gtg gca gct gta gtt gtt atg gct          394
Leu Ile Gly Asp Val Gln Met Pro Val Ala Ala Val Val Val Met Ala
        100                 105                 110 tgc agt cgt act gac tac ctg gag agg act att aaa tcc atc tta aaa          442
Cys Ser Arg Thr Asp Tyr Leu Glu Arg Thr Ile Lys Ser Ile Leu Lys
115                 120                 125                 130 tac caa aca tct gtt gca tca aaa tat cct ctt ttc ata tcc cag gat          490
```

-continued

| | | |
|---|---|---|
| Tyr Gln Thr Ser Val Ala Ser Lys Tyr Pro Leu Phe Ile Ser Gln Asp<br>                      135                    140                    145 | |
| gga tca aat cct gat gta aga aag ctt gct ttg agc tat ggt cag ctg<br>Gly Ser Asn Pro Asp Val Arg Lys Leu Ala Leu Ser Tyr Gly Gln Leu<br>               150                    155                  160 | 538 |
| acg tat atg cag cac ttg gat tat gaa cct gtg cat act gaa aga cca<br>Thr Tyr Met Gln His Leu Asp Tyr Glu Pro Val His Thr Glu Arg Pro<br>        165                    170                    175 | 586 |
| ggg gaa ctg gtt gca tac tac aag att gca cgt cat tac aag tgg gca<br>Gly Glu Leu Val Ala Tyr Tyr Lys Ile Ala Arg His Tyr Lys Trp Ala<br>180                    185                  190 | 634 |
| ttg gat cag ctg ttt cac aag cat aat ttt agc cgt gtt atc ata cta<br>Leu Asp Gln Leu Phe His Lys His Asn Phe Ser Arg Val Ile Ile Leu<br>195                    200                  205                  210 | 682 |
| gaa gat gat atg gaa att gct gct gat ttt ttt gac tat ttt gag gct<br>Glu Asp Asp Met Glu Ile Ala Ala Asp Phe Phe Asp Tyr Phe Glu Ala<br>               215                    220                  225 | 730 |
| gga gct act ctt ctt gac aga gac aag tcg att atg gct att tct tct<br>Gly Ala Thr Leu Leu Asp Arg Asp Lys Ser Ile Met Ala Ile Ser Ser<br>                    230                    235                  240 | 778 |
| tgg aat gac aat gga caa agg cag ttc gtc caa gat cct gat gct ctt<br>Trp Asn Asp Asn Gly Gln Arg Gln Phe Val Gln Asp Pro Asp Ala Leu<br>               245                    250                    255 | 826 |
| tac cgc tca gac ttt ttt cct ggt ctt gga tgg atg ctt tca aaa tca<br>Tyr Arg Ser Asp Phe Phe Pro Gly Leu Gly Trp Met Leu Ser Lys Ser<br>260                    265                  270 | 874 |
| act tgg tcc gaa cta tct cca aag tgg cca aag gct tac tgg gat gac<br>Thr Trp Ser Glu Leu Ser Pro Lys Trp Pro Lys Ala Tyr Trp Asp Asp<br>275                    280                  285                  290 | 922 |
| tgg cta agg ctg aaa gaa aat cac aga ggt cga caa ttt att cgc cca<br>Trp Leu Arg Leu Lys Glu Asn His Arg Gly Arg Gln Phe Ile Arg Pro<br>                    295                    300                  305 | 970 |
| gaa gtt tgc aga acg tac aat ttt ggt gag cat ggt tct agt ttg ggg<br>Glu Val Cys Arg Thr Tyr Asn Phe Gly Glu His Gly Ser Ser Leu Gly<br>               310                    315                  320 | 1018 |
| cag ttt ttt aag cag tat ctt gag cca att aag cta aat gat gtc cag<br>Gln Phe Phe Lys Gln Tyr Leu Glu Pro Ile Lys Leu Asn Asp Val Gln<br>        325                    330                    335 | 1066 |
| gtt gat tgg aag tca atg gac cta agt tac ctt ttg gag gac aac tat<br>Val Asp Trp Lys Ser Met Asp Leu Ser Tyr Leu Leu Glu Asp Asn Tyr<br>340                    345                  350 | 1114 |
| gtg aaa cac ttt ggc gac ttg gtt aaa aag gct aag ccc atc cac gga<br>Val Lys His Phe Gly Asp Leu Val Lys Lys Ala Lys Pro Ile His Gly<br>355                    360                  365                  370 | 1162 |
| gct gat gct gtt ttg aaa gca ttt aac ata gat ggt gat gtg cgt att<br>Ala Asp Ala Val Leu Lys Ala Phe Asn Ile Asp Gly Asp Val Arg Ile<br>                    375                    380                  385 | 1210 |
| cag tac aga gac caa cta gac ttt gaa gat atc gct cga cag ttt ggc<br>Gln Tyr Arg Asp Gln Leu Asp Phe Glu Asp Ile Ala Arg Gln Phe Gly<br>               390                    395                  400 | 1258 |
| att ttt gaa gaa tgg aag gat ggt gta cca cgg gca gca tat aaa ggg<br>Ile Phe Glu Glu Trp Lys Asp Gly Val Pro Arg Ala Ala Tyr Lys Gly<br>        405                    410                    415 | 1306 |
| ata gta gtt ttc cgg ttt caa aca tct aga cgt gtg ttc ctt gtt tcc<br>Ile Val Val Phe Arg Phe Gln Thr Ser Arg Arg Val Phe Leu Val Ser<br>420                    425                  430 | 1354 |
| cct gat tct ctt cga caa ctt gga gtt gaa gat act tag cgaagatatg<br>Pro Asp Ser Leu Arg Gln Leu Gly Val Glu Asp Thr *<br>435                    440                    445 | 1403 |

```
attggagcct gagcaacaat ttagacttat ttggtaggat acatttgaaa gagctgacac   1463
gaaaagtatg actaccagta gctacatgca acattttaat gttaatggaa ggaacccact   1523
gcttattgtt ggaatggatg aatcatcacc acatcctatt attcaagttt acaaacataa   1583
agaggaaatg ttgccctata aaacaaatt ttttgtttct aagaaggaac gttacgatta   1643
tgagcaactt tggcggccgc gaattc                                        1669
```

<210> SEQ ID NO 2
<211> LENGTH: 446
<212> TYPE: PRT
<213> ORGANISM: Solanum tuberosum

<400> SEQUENCE: 2

```
Met Arg Gly Asn Lys Phe Cys Phe Asp Leu Arg Tyr Leu Leu Val Val
 1               5                  10                  15

Ala Ala Leu Ala Phe Ile Tyr Ile Gln Met Arg Leu Phe Ala Thr Gln
            20                  25                  30

Ser Glu Tyr Val Asp Arg Leu Ala Ala Ala Ile Glu Ala Glu Asn His
        35                  40                  45

Cys Thr Ser Gln Thr Arg Leu Leu Ile Asp Lys Ile Ser Gln Gln Gln
    50                  55                  60

Gly Arg Val Val Ala Leu Glu Glu Gln Met Lys His Gln Asp Gln Glu
65                  70                  75                  80

Cys Arg Gln Leu Arg Ala Leu Val Gln Asp Leu Glu Ser Lys Gly Ile
                85                  90                  95

Lys Lys Leu Ile Gly Asp Val Gln Met Pro Val Ala Ala Val Val Val
            100                 105                 110

Met Ala Cys Ser Arg Thr Asp Tyr Leu Glu Arg Thr Ile Lys Ser Ile
        115                 120                 125

Leu Lys Tyr Gln Thr Ser Val Ala Ser Lys Tyr Pro Leu Phe Ile Ser
    130                 135                 140

Gln Asp Gly Ser Asn Pro Asp Val Arg Lys Leu Ala Leu Ser Tyr Gly
145                 150                 155                 160

Gln Leu Thr Tyr Met Gln His Leu Asp Tyr Glu Pro Val His Thr Glu
                165                 170                 175

Arg Pro Gly Glu Leu Val Ala Tyr Tyr Lys Ile Ala Arg His Tyr Lys
            180                 185                 190

Trp Ala Leu Asp Gln Leu Phe His Lys His Asn Phe Ser Arg Val Ile
        195                 200                 205

Ile Leu Glu Asp Asp Met Glu Ile Ala Ala Asp Phe Phe Asp Tyr Phe
    210                 215                 220

Glu Ala Gly Ala Thr Leu Leu Asp Arg Asp Lys Ser Ile Met Ala Ile
225                 230                 235                 240

Ser Ser Trp Asn Asp Asn Gly Gln Arg Gln Phe Val Gln Asp Pro Asp
                245                 250                 255

Ala Leu Tyr Arg Ser Asp Phe Phe Pro Gly Leu Gly Trp Met Leu Ser
            260                 265                 270

Lys Ser Thr Trp Ser Glu Leu Ser Pro Lys Trp Pro Lys Ala Tyr Trp
        275                 280                 285

Asp Asp Trp Leu Arg Leu Lys Glu Asn His Arg Gly Arg Gln Phe Ile
    290                 295                 300

Arg Pro Glu Val Cys Arg Thr Tyr Asn Phe Gly Glu His Gly Ser Ser
305                 310                 315                 320

Leu Gly Gln Phe Phe Lys Gln Tyr Leu Glu Pro Ile Lys Leu Asn Asp
```

```
                      325                 330                 335
Val Gln Val Asp Trp Lys Ser Met Asp Leu Ser Tyr Leu Leu Glu Asp
            340                 345                 350

Asn Tyr Val Lys His Phe Gly Asp Leu Val Lys Ala Lys Pro Ile
        355                 360                 365

His Gly Ala Asp Ala Val Leu Lys Ala Phe Asn Ile Asp Gly Asp Val
    370                 375                 380

Arg Ile Gln Tyr Arg Asp Gln Leu Asp Phe Glu Asp Ile Ala Arg Gln
385                 390                 395                 400

Phe Gly Ile Phe Glu Glu Trp Lys Asp Gly Val Pro Arg Ala Ala Tyr
                405                 410                 415

Lys Gly Ile Val Val Phe Arg Phe Gln Thr Ser Arg Arg Val Phe Leu
            420                 425                 430

Val Ser Pro Asp Ser Leu Arg Gln Leu Gly Val Glu Asp Thr
        435                 440                 445

<210> SEQ ID NO 3
<211> LENGTH: 1737
<212> TYPE: DNA
<213> ORGANISM: Nicotiana tabacum
<220> FEATURE:
<221> NAME/KEY: misc_feature
<222> LOCATION: (733)...(741)
<223> OTHER INFORMATION: function: Asn codon in this context is a
      potential glycosylation site;
      product: N-glycosylation consensus sequence;
      phenotype: N-glycans modulate protein properties;
<220> FEATURE:
<221> NAME/KEY: misc_feature
<222> LOCATION: (733)...(741)
<223> OTHER INFORMATION: standard_name: N-glycosylation site;
      label: pot-CHO;
      note: GnTI sequences from animals do not contain
      this feature.
<220> FEATURE:
<221> NAME/KEY: CDS
<222> LOCATION: (127)...(1467)
<223> OTHER INFORMATION: codon_start: 127;
      function: initiates complex N-glycans on secretory
      glycoproteins;
      EC_number: 2.4.1.101;
<220> FEATURE:
<221> NAME/KEY: CDS
<222> LOCATION: (127)...(1467)
<223> OTHER INFORMATION: product: beta-1,2-N-acetylglucosaminly-
      transferase I;
      evidence: EXPERIMENTAL;
      gene: cgl;
      standard_name: gntI;
<220> FEATURE:
<221> NAME/KEY: CDS
<222> LOCATION: (127)...(1467)
<223> OTHER INFORMATION: label: ORF;
      note: first gntI sequence from tobacco (unpublished).
<220> FEATURE:
<221> NAME/KEY: 5'UTR
<222> LOCATION: (15)...(126)
<220> FEATURE:
<221> NAME/KEY: 3'UTR
<222> LOCATION: (1468)...(1723)
<220> FEATURE:
<221> NAME/KEY: CDS
<222> LOCATION: (154)...(213)
<223> OTHER INFORMATION: function: membrane anchor (amino acids 10-29);
      product: hydrophobic amino acid stretch in GnTI;
      standard_name: membrane anchor of a type II golgi
      protein.
<220> FEATURE:
<221> NAME/KEY: misc_feature
<222> LOCATION: (1)...(14)
<223> OTHER INFORMATION: function: use for cloning the cDNA library in
```

```
      Lambda ZAPII;
      product: EcoRI/NotI-cDNA adapter;
      number: 1.
<220> FEATURE:
<221> NAME/KEY: misc_feature
<222> LOCATION: (1724)...(1737)
<223> OTHER INFORMATION: product: EcoRI/NotI-cDNA adapter;
      number: 2.

<400> SEQUENCE: 3
gaattcgcgg ccgccattga cttgatccta actgaacagg caaagtaaat ccagcgatga      60
aacactcata actgaacact gagagactat tcgctttctc ctaaagcctt caatcgaatt     120 cgcacg atg aga ggg aac aag ttt tgc tgt gat ttc cgg tac ctc ctc        168
       Met Arg Gly Asn Lys Phe Cys Cys Asp Phe Arg Tyr Leu Leu
         1               5                  10 atc ttg gct gct gtc gcc ttc atc tac aca cag atg cgg ctt ttt gcg       216
Ile Leu Ala Ala Val Ala Phe Ile Tyr Thr Gln Met Arg Leu Phe Ala
 15                  20                  25                  30 aca cag tca gaa tat gca gat cgc ctt gct gct gca att gaa gca gaa       264
Thr Gln Ser Glu Tyr Ala Asp Arg Leu Ala Ala Ala Ile Glu Ala Glu
                 35                  40                  45 aat cat tgt aca agc cag acc aga ttg ctt att gac cag att agc ctg       312
Asn His Cys Thr Ser Gln Thr Arg Leu Leu Ile Asp Gln Ile Ser Leu
             50                  55                  60 cag caa gga aga ata gtt gct ctt gaa gaa caa atg aag cgt cag gac       360
Gln Gln Gly Arg Ile Val Ala Leu Glu Glu Gln Met Lys Arg Gln Asp
         65                  70                  75 cag gag tgc cga caa tta agg gct ctt gtt cag gat ctt gaa agt aag       408
Gln Glu Cys Arg Gln Leu Arg Ala Leu Val Gln Asp Leu Glu Ser Lys
 80                  85                  90 ggc ata aaa aag ttg atc gga aat gta cag atg cca gtg gct gct gta       456
Gly Ile Lys Lys Leu Ile Gly Asn Val Gln Met Pro Val Ala Ala Val
 95                 100                 105                 110 gtt gtt atg gct tgc aat cgg gct gat tac ctg gaa aag act att aaa       504
Val Val Met Ala Cys Asn Arg Ala Asp Tyr Leu Glu Lys Thr Ile Lys
                115                 120                 125 tcc atc tta aaa tac caa ata tct gtt gcg tca aaa tat cct ctt ttc       552
Ser Ile Leu Lys Tyr Gln Ile Ser Val Ala Ser Lys Tyr Pro Leu Phe
            130                 135                 140 ata tcc cag gat gga tca cat cct gat gtc agg aag ctt gct ttg agc       600
Ile Ser Gln Asp Gly Ser His Pro Asp Val Arg Lys Leu Ala Leu Ser
        145                 150                 155 tat gat cag ctg acg tat atg cag cac ttg gat ttt gaa cct gtg cat       648
Tyr Asp Gln Leu Thr Tyr Met Gln His Leu Asp Phe Glu Pro Val His
    160                 165                 170 act gaa aga cca ggg gag ctg att gca tac tac aaa att gca cgt cat       696
Thr Glu Arg Pro Gly Glu Leu Ile Ala Tyr Tyr Lys Ile Ala Arg His
175                 180                 185                 190 tac aag tgg gca ttg gat cag ctg ttt tac aag cat aat ttt agc cgt       744
Tyr Lys Trp Ala Leu Asp Gln Leu Phe Tyr Lys His Asn Phe Ser Arg
                195                 200                 205 gtt atc ata cta gaa gat gat atg gaa att gcc cct gat ttt ttt gac       792
Val Ile Ile Leu Glu Asp Asp Met Glu Ile Ala Pro Asp Phe Phe Asp
            210                 215                 220 ttt ttt gag gct gga gct act ctt ctt gac aga gac aag tcg att atg       840
Phe Phe Glu Ala Gly Ala Thr Leu Leu Asp Arg Asp Lys Ser Ile Met
        225                 230                 235 gct att tct tct tgg aat gac aat gga caa atg cag ttt gtc caa gat       888
Ala Ile Ser Ser Trp Asn Asp Asn Gly Gln Met Gln Phe Val Gln Asp
    240                 245                 250
```

```
cct tat gct ctt tac cgc tca gat ttt ttt ccc ggt ctt gga tgg atg    936
Pro Tyr Ala Leu Tyr Arg Ser Asp Phe Phe Pro Gly Leu Gly Trp Met
255                 260                 265                 270 ctt tca aaa tct act tgg gac gaa tta tct cca aag tgg cca aag gct    984
Leu Ser Lys Ser Thr Trp Asp Glu Leu Ser Pro Lys Trp Pro Lys Ala
            275                 280                 285 tac tgg gac gac tgg cta aga ctc aaa gag aat cac aga ggt cga caa   1032
Tyr Trp Asp Asp Trp Leu Arg Leu Lys Glu Asn His Arg Gly Arg Gln
        290                 295                 300 ttt att cgc cca gaa gtt tgc aga aca tat aat ttt ggt gag cat ggt   1080
Phe Ile Arg Pro Glu Val Cys Arg Thr Tyr Asn Phe Gly Glu His Gly
    305                 310                 315 tct agt ttg ggg cag ttt ttc aag cag tat ctt gag cca att aaa cta   1128
Ser Ser Leu Gly Gln Phe Phe Lys Gln Tyr Leu Glu Pro Ile Lys Leu
320                 325                 330 aat gat gtc cag gtt gat tgg aag tca atg gac ctt agt tac ctt ttg   1176
Asn Asp Val Gln Val Asp Trp Lys Ser Met Asp Leu Ser Tyr Leu Leu
335                 340                 345                 350 gag gac aat tac gtg aaa cac ttt ggt gac ttg gtt aaa aag gct aag   1224
Glu Asp Asn Tyr Val Lys His Phe Gly Asp Leu Val Lys Lys Ala Lys
            355                 360                 365 ccc atc cat gga gct gat gct gtc ttg aaa gca ttt aac ata gat ggt   1272
Pro Ile His Gly Ala Asp Ala Val Leu Lys Ala Phe Asn Ile Asp Gly
        370                 375                 380 gat gtg cgt att cag tac aga gat caa cta gac ttt gaa aat atc gca   1320
Asp Val Arg Ile Gln Tyr Arg Asp Gln Leu Asp Phe Glu Asn Ile Ala
    385                 390                 395 cgg caa ttt ggc att ttt gaa gaa tgg aag gat ggt gta cca cgt gca   1368
Arg Gln Phe Gly Ile Phe Glu Glu Trp Lys Asp Gly Val Pro Arg Ala
400                 405                 410 gca tat aaa gga ata gta gtt ttc cgg tac caa acg tcc aga cgt gta   1416
Ala Tyr Lys Gly Ile Val Val Phe Arg Tyr Gln Thr Ser Arg Arg Val
415                 420                 425                 430 ttc ctt gtt ggc cat gat tcg ctt caa caa ctc gga att gaa gat act   1464
Phe Leu Val Gly His Asp Ser Leu Gln Gln Leu Gly Ile Glu Asp Thr
            435                 440                 445 taa caaagatatg attgcaggag cccgggcaaa attttgact tattgggtag        1517
 * gatgcatcga gctgacacta aaccatgatt ttaccagtta catacaacgt tttaatgtta  1577
tacggaggag ctcactgttc tagtgttgaa gggatatcgg cttcttagta ttggatgaat  1637
catcaacaca acctattatt ttaagtgttc agaacataaa gaggaaatgt agccctgtaa  1697
agactataca tgggaccatc ataatcgcgg ccgcgaattc                        1737

<210> SEQ ID NO 4
<211> LENGTH: 446
<212> TYPE: PRT
<213> ORGANISM: Nicotiana tabacum

<400> SEQUENCE: 4

Met Arg Gly Asn Lys Phe Cys Cys Asp Phe Arg Tyr Leu Leu Ile Leu
 1               5                  10                  15

Ala Ala Val Ala Phe Ile Tyr Thr Gln Met Arg Leu Phe Ala Thr Gln
            20                  25                  30

Ser Glu Tyr Ala Asp Arg Leu Ala Ala Ala Ile Glu Ala Glu Asn His
        35                  40                  45

Cys Thr Ser Gln Thr Arg Leu Leu Ile Asp Gln Ile Ser Leu Gln Gln
    50                  55                  60
```

```
Gly Arg Ile Val Ala Leu Glu Glu Gln Met Lys Arg Gln Asp Gln Glu
 65                  70                  75                  80

Cys Arg Gln Leu Arg Ala Leu Val Gln Asp Leu Glu Ser Lys Gly Ile
             85                  90                  95

Lys Lys Leu Ile Gly Asn Val Gln Met Pro Val Ala Ala Val Val Val
            100                 105                 110

Met Ala Cys Asn Arg Ala Asp Tyr Leu Glu Lys Thr Ile Lys Ser Ile
        115                 120                 125

Leu Lys Tyr Gln Ile Ser Val Ala Ser Lys Tyr Pro Leu Phe Ile Ser
    130                 135                 140

Gln Asp Gly Ser His Pro Asp Val Arg Lys Leu Ala Leu Ser Tyr Asp
145                 150                 155                 160

Gln Leu Thr Tyr Met Gln His Leu Asp Phe Glu Pro Val His Thr Glu
                165                 170                 175

Arg Pro Gly Glu Leu Ile Ala Tyr Tyr Lys Ile Ala Arg His Tyr Lys
            180                 185                 190

Trp Ala Leu Asp Gln Leu Phe Tyr Lys His Asn Phe Ser Arg Val Ile
        195                 200                 205

Ile Leu Glu Asp Asp Met Glu Ile Ala Pro Asp Phe Phe Asp Phe Phe
    210                 215                 220

Glu Ala Gly Ala Thr Leu Leu Asp Arg Asp Lys Ser Ile Met Ala Ile
225                 230                 235                 240

Ser Ser Trp Asn Asp Asn Gly Gln Met Gln Phe Val Gln Asp Pro Tyr
                245                 250                 255

Ala Leu Tyr Arg Ser Asp Phe Phe Pro Gly Leu Gly Trp Met Leu Ser
            260                 265                 270

Lys Ser Thr Trp Asp Glu Leu Ser Pro Lys Trp Pro Lys Ala Tyr Trp
        275                 280                 285

Asp Asp Trp Leu Arg Leu Lys Glu Asn His Arg Gly Arg Gln Phe Ile
    290                 295                 300

Arg Pro Glu Val Cys Arg Thr Tyr Asn Phe Gly Glu His Gly Ser Ser
305                 310                 315                 320

Leu Gly Gln Phe Phe Lys Gln Tyr Leu Glu Pro Ile Lys Leu Asn Asp
                325                 330                 335

Val Gln Val Asp Trp Lys Ser Met Asp Leu Ser Tyr Leu Leu Glu Asp
            340                 345                 350

Asn Tyr Val Lys His Phe Gly Asp Leu Val Lys Lys Ala Lys Pro Ile
        355                 360                 365

His Gly Ala Asp Ala Val Leu Lys Ala Phe Asn Ile Asp Gly Asp Val
    370                 375                 380

Arg Ile Gln Tyr Arg Asp Gln Leu Asp Phe Glu Asn Ile Ala Arg Gln
385                 390                 395                 400

Phe Gly Ile Phe Glu Glu Trp Lys Asp Gly Val Pro Arg Ala Ala Tyr
                405                 410                 415

Lys Gly Ile Val Val Phe Arg Tyr Gln Thr Ser Arg Arg Val Phe Leu
            420                 425                 430

Val Gly His Asp Ser Leu Gln Gln Leu Gly Ile Glu Asp Thr
    435                 440                 445

<210> SEQ ID NO 5
<211> LENGTH: 1854
<212> TYPE: DNA
<213> ORGANISM: Arabidopsis thaliana
<220> FEATURE:
<221> NAME/KEY: misc_feature
```

```
<222> LOCATION: (1185)...(1193)
<223> OTHER INFORMATION: function: Asn Codon is a potential
      glycosylation site;
      product: Consensus sequence for N-glycosylation;
      phenotype: N glycans modulate protein characteristics;
      standard name: N glycosylation site;
<220> FEATURE:
<221> NAME/KEY: misc_feature
<222> LOCATION: (1185)...(1193)
<223> OTHER INFORMATION: label: pot-CHO;
      note: absent in animal GnTI sequences.
<220> FEATURE:
<221> NAME/KEY: CDS
<222> LOCATION: (135)...(1469)
<223> OTHER INFORMATION: codon_start: 135;
      function: initiates complex N glycans on secretory glycoproteins;
      EC_number: 2.4.1.101;
<220> FEATURE:
<221> NAME/KEY: CDS
<222> LOCATION: (135)...(1469)
<223> OTHER INFORMATION: product: beta-1,2-N-acetyl glucosaminyl
      transferase I;
      evidence: EXPERIMENTAL;
      gene: cgl;
      standard_name: gntI;
<220> FEATURE:
<221> NAME/KEY: CDS
<222> LOCATION: (135)...(1469)
<223> OTHER INFORMATION: label: ORF;
      note: first gntI sequence from Arabidopsis
      (unpublished).
<220> FEATURE:
<221> NAME/KEY: 5'UTR
<222> LOCATION: (19)...(134)
<220> FEATURE:
<221> NAME/KEY: 3'UTR
<222> LOCATION: (1470)...(1848)
<220> FEATURE:
<221> NAME/KEY: CDS
<222> LOCATION: (157)...(215)
<223> OTHER INFORMATION: function: membrane anchor (amino acids 8-27);
      product: hydrophobic amino-acid region in GnTI;
      standard_name: membrane anchor of a Type II Golgi protein;
      note: identified by comparison with animal GnTI sequences.
<220> FEATURE:
<221> NAME/KEY: misc_feature
<222> LOCATION: (1)...(18)
<223> OTHER INFORMATION: function: for preparation of a cDNA library in
      Lambda ACT;
      product: XhoI-cDNA-Adaptor;
      number: 1.
<220> FEATURE:
<221> NAME/KEY: misc_feature
<222> LOCATION: (1849)...(1854)
<223> OTHER INFORMATION: product: XhoI-cDNA-Adaptor;
      number: 2.

<400> SEQUENCE: 5
ctcgaggcca cgaaggccac cgtttttgtt ataacgaacg acaccgtttc aaacaacttc     60
cttattagct agctccctcc cggcggcaaa caccagaaga tccaccgctt ttgatctggt    120
tgtttgtcgt cgat atg gcg agg atc tcg tgt gac ttg aga ttt ctt ctc     170
         Met Ala Arg Ile Ser Cys Asp Leu Arg Phe Leu Leu
           1               5                  10 atc ccg gca gct ttc atg ttc atc tac atc cag atg agg ctt ttc cag    218
Ile Pro Ala Ala Phe Met Phe Ile Tyr Ile Gln Met Arg Leu Phe Gln
        15                  20                  25 acg caa tca cag tat gca gat cgc ctc agt tcc gct atc gaa tct gag    266
Thr Gln Ser Gln Tyr Ala Asp Arg Leu Ser Ser Ala Ile Glu Ser Glu
    30                  35                  40 aac cat tgc act agt caa atg cga ggc ctc ata gat gaa gtt agc atc    314
Asn His Cys Thr Ser Gln Met Arg Gly Leu Ile Asp Glu Val Ser Ile
45                  50                  55                  60
```

```
aaa cag tcg cgg att gtt gcc ctc gaa gat atg aag aac cgc cag gac    362
Lys Gln Ser Arg Ile Val Ala Leu Glu Asp Met Lys Asn Arg Gln Asp
            65                  70                  75 gaa gaa ctt gtg cag ctt aag gat cta atc cag acg ttt gaa aaa aaa    410
Glu Glu Leu Val Gln Leu Lys Asp Leu Ile Gln Thr Phe Glu Lys Lys
                80                  85                  90 gga ata gca aaa ctc act caa ggt gga cag atg cct gtg gct gct gta    458
Gly Ile Ala Lys Leu Thr Gln Gly Gly Gln Met Pro Val Ala Ala Val
                    95                 100                 105 gtg gtt atg gcc tgc agt cgt gca gac tat ctt gaa agg act gtt aaa    506
Val Val Met Ala Cys Ser Arg Ala Asp Tyr Leu Glu Arg Thr Val Lys
        110                 115                 120 tca gtt tta aca tat caa act ccc gtt gct tca aaa tat cct cta ttt    554
Ser Val Leu Thr Tyr Gln Thr Pro Val Ala Ser Lys Tyr Pro Leu Phe
125                 130                 135                 140 ata tct cag gat gga tct gat caa gct gtc aag agc aag tca ttg agc    602
Ile Ser Gln Asp Gly Ser Asp Gln Ala Val Lys Ser Lys Ser Leu Ser
                    145                 150                 155 tat aat caa tta aca tat atg cag cac ttg gat ttt gaa cca gtg gtc    650
Tyr Asn Gln Leu Thr Tyr Met Gln His Leu Asp Phe Glu Pro Val Val
            160                 165                 170 act gaa agg cct ggt gaa ctg act gcg tac tac aag att gca cgt cac    698
Thr Glu Arg Pro Gly Glu Leu Thr Ala Tyr Tyr Lys Ile Ala Arg His
        175                 180                 185 tac aag tgg gca ctg gac cag ttg ttt tac aaa cac aaa ttt agt cga    746
Tyr Lys Trp Ala Leu Asp Gln Leu Phe Tyr Lys His Lys Phe Ser Arg
    190                 195                 200 gtg att ata cta gaa gac gat atg gaa att gct cca gac ttc ttt gat    794
Val Ile Ile Leu Glu Asp Asp Met Glu Ile Ala Pro Asp Phe Phe Asp
205                 210                 215                 220 tac ttt gag gct gca gct agt ctc atg gat agg gat aaa acc att atg    842
Tyr Phe Glu Ala Ala Ala Ser Leu Met Asp Arg Asp Lys Thr Ile Met
                225                 230                 235 gct gct tca tca tgg aat gat aat gga cag aag cag ttt gtg cat gat    890
Ala Ala Ser Ser Trp Asn Asp Asn Gly Gln Lys Gln Phe Val His Asp
                    240                 245                 250 ccc tat gcg cta tac cga tca gat ttt ttt cct ggc ctt ggg tgg atg    938
Pro Tyr Ala Leu Tyr Arg Ser Asp Phe Phe Pro Gly Leu Gly Trp Met
            255                 260                 265 ctc aag aga tcg act tgg gat gag tta tca cca aag tgg cca aag gct    986
Leu Lys Arg Ser Thr Trp Asp Glu Leu Ser Pro Lys Trp Pro Lys Ala
270                 275                 280 tac tgg gat gat tgg ctg aga cta aag gaa aac cat aaa ggc cgc caa   1034
Tyr Trp Asp Asp Trp Leu Arg Leu Lys Glu Asn His Lys Gly Arg Gln
285                 290                 295                 300 ttc att gca ccg gaa gtc tgt aga aca tac aat ttt ggt gaa cat ggg   1082
Phe Ile Ala Pro Glu Val Cys Arg Thr Tyr Asn Phe Gly Glu His Gly
                305                 310                 315 tct agt ttg gga cag ttt ttc agt cag tat ctg gaa cct ata aag cta   1130
Ser Ser Leu Gly Gln Phe Phe Ser Gln Tyr Leu Glu Pro Ile Lys Leu
                    320                 325                 330 aac gat gtg acg gtt gac tgg aaa gca aag gac ctg gga tac ctg aca   1178
Asn Asp Val Thr Val Asp Trp Lys Ala Lys Asp Leu Gly Tyr Leu Thr
            335                 340                 345 gag gga aac tat acc aag tac ttt tct ggc tta gtg aga caa gca cga   1226
Glu Gly Asn Tyr Thr Lys Tyr Phe Ser Gly Leu Val Arg Gln Ala Arg
        350                 355                 360 cca att caa ggt tct gac ctt gtc tta aag gct caa aac ata aag gat   1274
Pro Ile Gln Gly Ser Asp Leu Val Leu Lys Ala Gln Asn Ile Lys Asp
365                 370                 375                 380
```

```
gat gat cgt atc cgg tat aaa gac caa gta gag ttt gaa cgc att gca    1322
Asp Asp Arg Ile Arg Tyr Lys Asp Gln Val Glu Phe Glu Arg Ile Ala
            385                 390                 395 ggg gaa ttt ggt ata ttt gaa gaa tgg aag gat ggt gtg cca cga aca    1370
Gly Glu Phe Gly Ile Phe Glu Glu Trp Lys Asp Gly Val Pro Arg Thr
    400                 405                 410 gca tat aaa gga gta gtg gtg ttt cga atc cag aca aca aga cgt gta    1418
Ala Tyr Lys Gly Val Val Val Phe Arg Ile Gln Thr Thr Arg Arg Val
            415                 420                 425 ttc ctg gtt ggg cca gat tct gta atg cag ctt gga att cga aat tcc    1466
Phe Leu Val Gly Pro Asp Ser Val Met Gln Leu Gly Ile Arg Asn Ser
        430                 435                 440 tga tgcaaaacat atgaaaggaa aagaagattt tggaccgcat gcagcctcct         1519
 * tctagcagct gttaggttgt attgttattt atggatgagt ttgtagagcg gtggggttaa  1579
ctttaacagc aaggaagctc tggtgaccag gctgattggc ttagaagtta tgggaacccc  1639 ttgaagggt cagggttaaa tatatttcag ttgttttatt agtgattatc ttgtgggtaa   1699
cttatacgaa tgcaaatcat tctatgcagt ttttcttcgt cccacttgtt ttggcttctc  1759
tattgctagt gtacatatct cttcaaacat gtactaaata atgcgtgttg cttcaaagaa  1819 gtaacttta ttaaaaaaaa aaaaaaaaac tcgag                              1854

<210> SEQ ID NO 6
<211> LENGTH: 444
<212> TYPE: PRT
<213> ORGANISM: Arabidopsis thaliana

<400> SEQUENCE: 6

Met Ala Arg Ile Ser Cys Asp Leu Arg Phe Leu Leu Ile Pro Ala Ala
  1               5                  10                  15

Phe Met Phe Ile Tyr Ile Gln Met Arg Leu Phe Gln Thr Gln Ser Gln
             20                  25                  30

Tyr Ala Asp Arg Leu Ser Ser Ala Ile Glu Ser Glu Asn His Cys Thr
         35                  40                  45

Ser Gln Met Arg Gly Leu Ile Asp Glu Val Ser Ile Lys Gln Ser Arg
     50                  55                  60

Ile Val Ala Leu Glu Asp Met Lys Asn Arg Gln Asp Glu Glu Leu Val
 65                  70                  75                  80

Gln Leu Lys Asp Leu Ile Gln Thr Phe Glu Lys Lys Gly Ile Ala Lys
                 85                  90                  95

Leu Thr Gln Gly Gly Gln Met Pro Val Ala Ala Val Val Met Ala
            100                 105                 110

Cys Ser Arg Ala Asp Tyr Leu Glu Arg Thr Val Lys Ser Val Leu Thr
        115                 120                 125

Tyr Gln Thr Pro Val Ala Ser Lys Tyr Pro Leu Phe Ile Ser Gln Asp
    130                 135                 140

Gly Ser Asp Gln Ala Val Lys Ser Lys Ser Leu Ser Tyr Asn Gln Leu
145                 150                 155                 160

Thr Tyr Met Gln His Leu Asp Phe Glu Pro Val Val Thr Glu Arg Pro
                165                 170                 175

Gly Glu Leu Thr Ala Tyr Tyr Lys Ile Ala Arg His Tyr Lys Trp Ala
            180                 185                 190

Leu Asp Gln Leu Phe Tyr Lys His Lys Phe Ser Arg Val Ile Ile Leu
        195                 200                 205
```

```
Glu Asp Asp Met Glu Ile Ala Pro Asp Phe Phe Asp Tyr Phe Glu Ala
    210                 215                 220

Ala Ala Ser Leu Met Asp Arg Asp Lys Thr Ile Met Ala Ala Ser Ser
225                 230                 235                 240

Trp Asn Asp Asn Gly Gln Lys Gln Phe Val His Asp Pro Tyr Ala Leu
                245                 250                 255

Tyr Arg Ser Asp Phe Phe Pro Gly Leu Gly Trp Met Leu Lys Arg Ser
            260                 265                 270

Thr Trp Asp Glu Leu Ser Pro Lys Trp Pro Lys Ala Tyr Trp Asp Asp
        275                 280                 285

Trp Leu Arg Leu Lys Glu Asn His Lys Gly Arg Gln Phe Ile Ala Pro
    290                 295                 300

Glu Val Cys Arg Thr Tyr Asn Phe Gly Glu His Gly Ser Ser Leu Gly
305                 310                 315                 320

Gln Phe Phe Ser Gln Tyr Leu Glu Pro Ile Lys Leu Asn Asp Val Thr
                325                 330                 335

Val Asp Trp Lys Ala Lys Asp Leu Gly Tyr Leu Thr Glu Gly Asn Tyr
            340                 345                 350

Thr Lys Tyr Phe Ser Gly Leu Val Arg Gln Ala Arg Pro Ile Gln Gly
        355                 360                 365

Ser Asp Leu Val Leu Lys Ala Gln Asn Ile Lys Asp Asp Arg Ile
    370                 375                 380

Arg Tyr Lys Asp Gln Val Glu Phe Glu Arg Ile Ala Gly Glu Phe Gly
385                 390                 395                 400

Ile Phe Glu Glu Trp Lys Asp Gly Val Pro Arg Thr Ala Tyr Lys Gly
                405                 410                 415

Val Val Val Phe Arg Ile Gln Thr Thr Arg Arg Val Phe Leu Val Gly
            420                 425                 430

Pro Asp Ser Val Met Gln Leu Gly Ile Arg Asn Ser
        435                 440

<210> SEQ ID NO 7
<211> LENGTH: 24
<212> TYPE: DNA
<213> ORGANISM: Artificial Sequence
<220> FEATURE:
<223> OTHER INFORMATION: Primer for cloning plant genes
<220> FEATURE:
<221> NAME/KEY: misc_feature
<222> LOCATION: (6)...(12)
<223> OTHER INFORMATION: n at positions 6, 9 & 12 = inosine.

<400> SEQUENCE: 7
tgygynwsng cntggmayga yaay                                              24

<210> SEQ ID NO 8
<211> LENGTH: 24
<212> TYPE: DNA
<213> ORGANISM: Artificial Sequence
<220> FEATURE:
<223> OTHER INFORMATION: Primer for cloning plant genes
<220> FEATURE:
<221> NAME/KEY: misc_feature
<222> LOCATION: (4)...(10)
<223> OTHER INFORMATION: n at positions 4, 7, & 10 = inosine.
<220> FEATURE:
<221> NAME/KEY: misc_feature
<222> LOCATION: 13
<223> OTHER INFORMATION: n = a, c, g, or t.

<400> SEQUENCE: 8
```

```
ccanccntrn ccngsraara artc                                          24

<210> SEQ ID NO 9
<211> LENGTH: 14
<212> TYPE: PRT
<213> ORGANISM: Artificial Sequence
<220> FEATURE:
<223> OTHER INFORMATION: Primer for cloning plant genes
<220> FEATURE:
<221> NAME/KEY: VARIANT
<222> LOCATION: 2
<223> OTHER INFORMATION: Xaa = Arg or Met.
<220> FEATURE:
<221> NAME/KEY: VARIANT
<222> LOCATION: 9
<223> OTHER INFORMATION: Xaa = Asp or Tyr.

<400> SEQUENCE: 9

Gln Xaa Gln Phe Val Gln Asp Pro Xaa Ala Leu Tyr Arg Ser
 1               5                  10

<210> SEQ ID NO 10
<211> LENGTH: 48
<212> TYPE: DNA
<213> ORGANISM: Artificial Sequence
<220> FEATURE:
<223> OTHER INFORMATION: Primer for cloning plant genes

<400> SEQUENCE: 10
atcggaaagc ttgatcccc agtggcrgct gtagttgtta tggcttgc                 48

<210> SEQ ID NO 11
<211> LENGTH: 27
<212> TYPE: DNA
<213> ORGANISM: Artificial Sequence
<220> FEATURE:
<223> OTHER INFORMATION: Primer for cloning plant genes

<400> SEQUENCE: 11
ggccccccct cgaggtcgac ggtatcg                                       27

<210> SEQ ID NO 12
<211> LENGTH: 51
<212> TYPE: DNA
<213> ORGANISM: Artificial Sequence
<220> FEATURE:
<223> OTHER INFORMATION: Primer for cloning plant genes

<400> SEQUENCE: 12
gggcctctag actccagagc yactactctt ccttgctgct ggctaatctt g            51

<210> SEQ ID NO 13
<211> LENGTH: 40
<212> TYPE: DNA
<213> ORGANISM: Artificial Sequence
<220> FEATURE:
<223> OTHER INFORMATION: Primer for cloning plant genes

<400> SEQUENCE: 13
catggatccc tcgagaagcg tcaggaccag gagtgccggc                         40

<210> SEQ ID NO 14
<211> LENGTH: 37
<212> TYPE: DNA
<213> ORGANISM: Artificial Sequence
<220> FEATURE:
<223> OTHER INFORMATION: Primer for cloning plant genes
```

```
<400> SEQUENCE: 14
atcccgggat ccgctacgta tcttcaactc caagttg                                37
```